(12) United States Patent
Takai et al.

(10) Patent No.: US 7,173,157 B2
(45) Date of Patent: Feb. 6, 2007

(54) METHOD FOR PRODUCING AN ALLYL COMPOUND

(75) Inventors: Masaki Takai, Kanagawa (JP); Yoshiyuki Tanaka, Kanagawa (JP)

(73) Assignee: Mitsubishi Chemical Corporation, Tokyo (JP)

( * ) Notice: Subject to any disclaimer, the term of this patent is extended or adjusted under 35 U.S.C. 154(b) by 445 days.

(21) Appl. No.: 10/650,697

(22) Filed: Aug. 29, 2003

(65) Prior Publication Data

US 2005/0075518 A1 Apr. 7, 2005

(30) Foreign Application Priority Data

Aug. 30, 2002 (JP) ............................. 2002-252901
Sep. 5, 2002 (JP) ............................. 2002-260452
Sep. 6, 2002 (JP) ............................. 2002-261870

(51) Int. Cl.
*C07C 41/06* (2006.01)
*C07C 69/76* (2006.01)

(52) U.S. Cl. ...................... 568/687; 560/113

(58) Field of Classification Search ............... 560/113; 568/657, 687, 690
See application file for complete search history.

(56) References Cited

U.S. PATENT DOCUMENTS 4,613,703 A * 9/1986 Hefner, Jr. .................. 568/640
6,300,515 B1 10/2001 Retboll et al.

FOREIGN PATENT DOCUMENTS

JP   2-172924       7/1990
WO   WO 02/40491    5/2002

OTHER PUBLICATIONS

U.S. Appl. No. 10/648,210, filed Aug. 27, 2003, Takai et al.
U.S. Appl. No. 10/650,697, filed Aug. 29, 2003, Takai et al.
U.S. Appl. No. 10/649,767, filed Aug. 28, 2003, Takai et al.
M. Dieguez, et al., Chem. Commun, pp. 1132-1133, "Diphosphites as a Promising New Class of Ligands in PD-Catalysed Asymmetric Allylic Alkylation", 2001.
O. Pamies. et al., J. Org. Chem., vol. 66, No. 26, pp. 8867-8871, "Modular Furanoside Phosphite Ligands for Asymmetric PD-Catalyzed Allylic Substitution", 2001.
K. Pachamuthu, et al., Tetrahedron Letters, vol. 39, pp. 5439-5442, "Palladium Catalysed Regio and Stereoselective Reduction of Baylis-Hillman Coupling Products Derived Allylic Acetates", May 19, 1998.

J. Tsuji, et al., Bulletin of the Chemical Society of Japan, vol. 49, No. 6, pp. 1701-1702, "Preparation of Matsutake Alchohol (1-Octen-3-Ol) From a Butadiene Telomer", Jun. 1976, (p. 1702 will be filed later).
J. Ross, et al., Organometallics, vol. 20, No. 1, pp. 138-142 "Ligand Effects in Palladium-Catalyzed Allylic Alkylation in Ionic Liquids", 2001.
N. Yoshimura, et al., Nihon Kagaku Gakkaishi, The Chemical Society of Japan, No. 2, pp. 119-127, "New Processes for 1-Octanol and Various Diols by Noble Metal Complex Catalysts", 1993.

* cited by examiner

*Primary Examiner*—Rosalynd Keys
(74) *Attorney, Agent, or Firm*—Oblon, Spivak, McClelland, Maier & Neustadt, P.C.

(57) ABSTRACT

An allyl compound having a formula different from that of an allyl starting compound is prepared by a process of reacting the allyl starting compound with a nucleophilic agent in the presence of a catalyst containing at least one transition metal compound containing a transition metal selected from the group consisting of elements belonging to Group 8 to Group 10 of the Periodic Table and at least one bidentate coordinated phosphite compound selected from the group consisting of compounds having the following formulae (I) to (III):

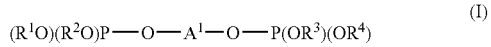

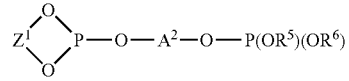

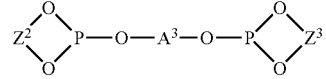

wherein $A^1$ to $A^3$ are respectively independently a diarylene group having a branched alkyl group at the ortho-position, $R^1$ to $R^6$ are respectively independently an alkyl group which may have a substituent or an aryl group which may have a substituent (including a heterocyclic compound forming an aromatic 6Π electron cloud on the upper and lower sides of the ring, hereinafter the same), and $Z^1$ to $Z^3$ are respectively independently an optionally substituted alkylene group, an optionally substituted arylene group, an optionally substituted alkylene-arylene group or an optionally substituted diarylene group.

13 Claims, No Drawings

METHOD FOR PRODUCING AN ALLYL COMPOUND

BACKGROUND OF THE INVENTION

1. Field of the Invention

The present invention relates to a method for producing a new allyl compound different from an allyl starting material compound by reacting the allyl starting material compound with a nucleophilic agent in the presence of a catalyst comprising a transition metal compound and a phosphite compound, and an allyl compound produced thereby.

2. Prior Arts

Various kinds of new allyl compounds can be synthesized by carrying out a catalytic reaction using a transition metal compound and using an allyl compound as a starting material. This reaction proceeds as illustrated in the following reaction formula, wherein an allyl starting material compound having an eliminating group X is Π-coordinated and oxidatively added to a transition metal compound to form a Π-allyl complex having three carbons of the allyl part bonded to a metal and the terminal allyl carbon of the Π-allyl complex is attacked by a nucleophilic agent expressed by Nu—H or Nu⁻.

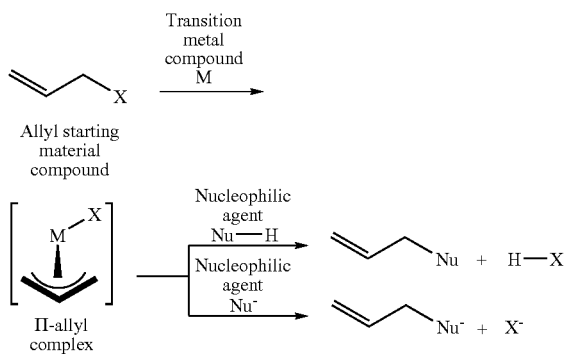

The synthesizing reaction of an allyl compound is generally fully described in "Palladium Reagents and Catalysts—Innovations in Organic Synthesis—" published by John Wiley & Sons Company, and various products in a form of allylated nucleophilic agent can be obtained by electing a kind of a nucleophilic agent in the reaction.

For example, when the nucleophilic agent is malonic acid diester, malonic acid diester having an allyl group bonded is formed (allylic alkylation reaction), and when the nucleophilic agent is a primary or secondary amine, allyl amines are formed (allylic amination reaction) and when the nucleophilic agent is phenol or carboxylic acid, allyl phenyl ether or carboxylic acid allyl ester are respectively formed.

On the other hand, as a transition metal compound for a catalyst, a palladium compound is most famous, but a catalytic reaction of an allyl compound with a ruthenium compound, a nickel compound, an iridium compound or the like is also known. Further, there have been developed various ligands to improve a catalytic activity, a regioselectivity of reaction or an enantioselectivity by being coordinated to such transition metal compounds.

When carrying out allylation reaction with the above-mentioned catalyst on an industrial scale, it is strongly demanded to improve a catalyst reactivity in order to reduce a catalyst cost by reducing an amount of catalyst used or to reduce a manufacturing cost by making a reactor size smaller. Further, in order to reduce the cost of a catalyst itself, it is necessary to reduce a production cost of a ligand used. From this viewpoint, such a bidentate coordinated phosphite ligand as described in "Chem. Commun., 2001, p 1132" and "J. Org. Chem., 2001, 66, p 8867" is not suitable for a high temperature reaction achieving a high catalyst activity since its crosslinking part comprises glucose and a ligand does not have a satisfactory thermal stability.

Also, recently reported WO2002/040491 publication discloses a reaction of an allyl ester starting material compound with a carbon nucleophilic agent (allylic alkylation reaction) or with a nitrogen nucleophilic agent (allylic amination reaction) by using a bidentate coordinated phosphite ligand having an axial asymmetry at the biphenol part of crosslinking portion, but does not illustrate an actual example of allylation reaction using the bidentate coordinated phosphite ligand and does not disclose a structure of the phosphite compound to be suitably used for the allylation reaction.

When carrying out allylation reaction using the above-mentioned catalyst on an industrial scale, it is strongly demanded to improve a reactivity in order to reduce an amount of expensive palladium used, which is a noble metal, or to make a reactor size smaller, thereby reducing a manufacturing cost. As a method for improving the reactivity, there is a method for having a counter cation of a nucleophilic agent present in the reaction system. As its effect, a nucleophilic agent forming a pair or a coexistent state with such a counter cation increases its nucleophilic attacking force, thereby improving the reactivity.

As some examples, a reaction of cyclopentadiene monoxide and an acetic acid anion is reported in "Organic Syntheses, 1998, 67, p 114", and in order to improve the reactivity, a sodium ion is used as a counter cation for acetic anion in this reaction. However, when such an alkali metal is a counter cation, +1 valent charge is concentrated on one small metal ion, and accordingly there is a tendency of forming a strong ion pair with a nucleophilic agent of a counter anion. Consequently, the attacking force of such a nucleophilic agent is not sufficiently high.

For example, it is reported in "Tetrahedron Lett., 1998, 39, p 5439" that an allyl starting material compound and a formic acid anion are reacted by using a palladium catalyst comprising a triisopropyl phosphite ligand of trialkyl type monodentate phosphite in the presence of ammonium comprising triethylamine having a proton coordinate-bonded, but this reaction is a reaction different from a reaction of an ordinary allyl starting material compound and a nucleophilic agent. That is, the formic acid anion does not form allyl formate by attacking a Π-allyl complex as an intermediate but is coordinated to palladium, and carbon dioxide is eliminated and a hydride formed as this result reacts with the Π-allyl complex to provide a product of a structure having the allyl starting material reduced.

As mentioned above, in order to produce various allyl compounds by reaction of an allyl starting material compound and a nucleophilic agent on an industrial scale, it is important to reduce a catalyst cost. As a method for reducing the catalyst cost, there are provided a method for reducing an amount of a catalyst used, a method for reducing a ligand cost by using a cheap ligand, a method for recycling a ligand by using a stable ligand and the like, but when using a phosphine type ligand which is relatively hardly synthesized, as a ligand, or when using a bidentate ligand having an axial asymmetry or a complicated bidentate ligand such as P—N, P—O, P—S or N—S, a manufacturing cost of the ligand becomes high. Also, in a case of a bidentate phosphite ligand which can be relatively easily synthesized, if a carbon atom of P—O—C bond at the crosslinking part is a sp³ carbon of an alkyl group, a satisfactory thermal stability can not be obtained and it is difficult to be used for carrying out a highly active reaction at a high temperature. Accordingly, there has been demanded development of a new catalyst system using a ligand having a satisfactory thermal stability and achieving a high activity, which can be easily prepared.

The present invention has been made in order to solve the above-mentioned problems. Thus, an object of the present invention is to provide a method for producing an industrially advantageous allyl compound by using a new catalyst system having an excellent thermal stability and achieving a high activity, which can be easily prepared, thereby efficiently producing various allyl compounds.

The present inventors have intensively studied to develop a catalyst system capable of efficiently proceeding an intermolecular reaction of a nucleophilic agent and various allyl starting material compounds, and have discovered that a satisfactory catalyst having a high activity can be obtained by combining a transition metal compound of Group 8 to Group 10 of the Periodic Table with a specific bidentate phosphite ligand having a branched alkyl group at the ortho position of an aryl group and a carbon atom of P—O—C bond at a crosslinking part, the carbon atom of which is a sp² carbon derived from an aryl group. The present invention has been accomplished on the basis of this discovery.

SUMMARY OF THE INVENTION

That is, the essential feature of the present invention resides in a method for producing a new allyl compound having a compositional formula different from that of an allyl starting material compound, which comprises reacting the allyl starting material compound with a nucleophilic agent in the presence of a catalyst containing at least one transition metal compound containing a transition metal selected from the group consisting of transition metals belonging to Group 8 to Group 10 of the Periodic Table and at least one bidentate coordinated phosphite compound selected from the group consisting of compounds having structures of the following formulae (I) to (III):

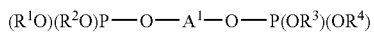  (I)

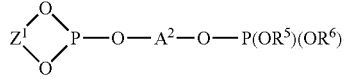  (II)

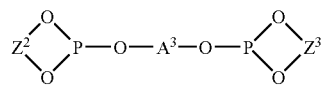  (III)

wherein $A^1$ to $A^3$ are respectively independently a diarylene group having a branched alkyl group at the ortho-position, $R^1$ to $R^6$ are respectively independently an alkyl group which may have a substituent or an aryl group which may have a substituent (including a heterocyclic compound forming an aromatic 6Π electron cloud on the upper and lower sides of the ring, hereinafter the same), and $Z^1$ to $Z^3$ are respectively independently an alkylene group which may have a substituent, an arylene group which may have a substituent, an alkylene-arylene group which may have a substituent or a diarylene group which may have a substituent.

DETAILED DESCRIPTION OF THE PREFERRED EMBODIMENTS

Hereinafter, the present invention is described in more details.

A method for producing an allyl compound in accordance with the present invention (hereinafter referred to as "production method of the present invention") produces a new allyl compound having a compositional formula different from an allyl starting material compound by reacting the allyl starting material compound with a nucleophilic agent in the presence of a catalyst containing the following specific transition metal compound and the following bidentate coordinated phosphite compound having a specific structure.

First, the allyl starting material compound used in the production method of the present invention is explained hereinafter. The allyl starting material compound is not specially limited so long as it has an allyl group and an eliminating group in a molecule, but has a total molecular weight of at most 1,500 (about at most 100 carbon atoms), and it is preferable that under reaction conditions, a part or all of the allyl starting material compound is soluble in a solvent, compatible with an oxygen nucleophilic agent, or meltable by melting with heat. Among them, a preferable example is a compound having such a structure as expressed by the following formula (a) wherein an eliminating group expressed by X is bonded to an allyl group having a group expressed by $R^a$ to $R^e$. The eliminating group means an atom or an atom group which is bonded to carbon of a substrate structure (allyl structure in the present invention) as a matrix and is generally an electron withdrawing group and is eliminated from the substrate molecule having an electron pair.

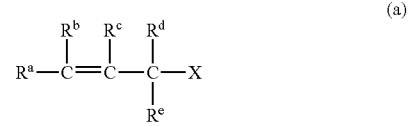  (a)

In the above formula (a), $R^a$ to $R^e$ are respectively independently a hydrogen atom, a halogen atom, a hydroxy group, an amino group, a formyl group, a chain-like or cyclic alkyl group, an aryl group, an alkoxy group, an aryloxy group, an alkylthio group, an arylthio group, an amide group, an acyl group or an acyloxy group (in the present specification, the aryl group includes a heterocyclic compound forming an aromatic 6Π electron cloud on the upper and lower parts of the ring). The above illustrated groups may further have a substituent. Examples of the substituent are not specially limited so long as they do not affect adversely the reaction system, but preferable examples include a halogen atom, a hydroxy group, an amino group, a formyl group, an alkyl group, an aryl group, an alkoxy group, an aryloxy group, an alkylthio group, an arylthio group, an amide group, an acyl group or an acyloxy group.

Preferable examples of the above $R^a$ to $R^e$ include a hydrogen atom, a halogen atom, a hydroxy group, an amino group, a chain-like or cyclic alkyl group which may be substituted with the above substituents, an aryl group which may be substituted with the above substituents, an alkoxy group which may be substituted with the above substituents, an aryloxy group which may be substituted with the above substituents, an alkylthio group, an arylthio group, an acyl group or an acyloxy group, and more preferable examples include a hydrogen atom, a halogen atom, a hydroxy group, an amino group, a chain-like or cyclic alkyl group which may be substituted with the above substituents, an aryl group which may be substituted with the above substituents, an alkoxy group, an arylalkoxy group, an aryloxy group, an alkylaryloxy group, an alkylthio group, an arylthio group, an acyl group or an acyloxy group.

The carbon number of $R^a$ to $R^e$ is generally at most 40, preferably at most 30, more preferably at most 20. When $R^a$ to $R^e$ is a group containing a carbon chain, the group may have at least one carbon-carbon double bond or triple bond in the carbon chain.

Among the above illustrated groups, particularly preferable $R^a$ to $R^e$ are respectively independently a hydrogen atom, a substituted or unsubstituted alkyl group or a substituted or unsubstituted aryl group.

Also, a group adversely affecting the reaction system is a material poisoning a catalyst such as a group containing conjugated diene, a material oxidizing and decomposing a phosphite compound such as a group containing peroxide or the like. Accordingly, in the present specification, a group "having no adverse affect on the reaction system" means to exclude these groups adversely affecting the reaction system.

On the other hand, examples of the eliminating group X include a halogen atom, a hydroxy group, a nitro group, an amino group expressed by $R'_2N-$, a sulfonyl group expressed by $RSO_2-$, a sulfonate group expressed by $RSO_2O-$, an acyloxy group expressed by $RC(=O)O-$, a carbonate group expressed by $R'OC(=O)O-$, a carbamate group expressed by $R'NHC(=O)O-$, a phosphate group expressed by $(R'O)_2P(=O)O-$, or an alkoxy group or an aryloxy group expressed by $RO-$. In the above formulae, R is a monovalent organic group and R' is a hydrogen atom or a monovalent organic group. The kind of the organic group is not specially limited so long as it does not adversely affect the reaction system, but preferable examples include an alkyl group or an aryl group. When R is an organic group, its carbon number is generally from 1 to 40, preferably from 1 to 30, more preferably from 1 to 20. When the eliminating group X is a group containing a carbon chain, it may have at least one carbon-carbon double or triple bond in a carbon chain.

Among the above illustrated examples, X is preferably a hydroxyl group, an acyloxy group having a structure expressed by $-C(=O)O-$, a carbonate group, a carbamate group, a phosphate group having a structure expressed by $=P(=O)-$ or a sulfonate group having a structure expressed by $-S(=O)_2O-$, and particularly preferable examples include a hydroxyl group, an acyloxy group and a carbonate group. Examples of the acyloxy group include a $C_1-C_6$ acyloxy group such as an acetoxy group, a propionyloxy group, a butyryloxy group or an isobutyryloxy group. Examples of the carbonate group include a $C_1-C_6$ alkylcarbonate group such as a methylcarbonate group, an ethylcarbonate group or a $C_6-C_{12}$ arylcarbonate group such as a phenylcarbonate group. A particularly preferable example of X is a hydroxyl group and an acyloxy group, and the most preferable example of X is an acetoxy group.

Among the above $R^a$ to $R^e$ and X, at least two optional groups may be bonded to each other to form at least one cyclic structure. However, when X is contained in a stable cyclic structure, it is not preferable since X is hardly eliminated. The number of cyclic structures is not specially limited, but is generally from 0 to 3, preferably from 0 to 2, particularly preferably from 0 or 1. Also, the number of atoms forming each ring is not specially limited, but is usually 3 to 10-membered ring, preferably 4 to 9-membered ring, particularly preferably 5 to 7-membered ring. When a plurality of rings are present, these rings may be partly commonly owned to form a condensed ring structure.

When at least two groups of $R^a$ to $R^e$ and X are bonded to form a cyclic structure, its carbon number is usually 0 to 40×p, preferably 0 to 30×p, more preferably 0 to 20×p, wherein p is a number of groups participating in the formation of the ring structure.

Examples of the allyl starting material compound expressed by the above formula (a) include preferably halogenated allyls, allyl alcohols, allylamines, allyl sulfones, allyl sulfonates, allyl esters of carboxylic acids, allyl carbonates, allyl carbamates, allyl esters of phosphoric acid, allyl ethers, vinyl ethylene oxides, and the like.

Examples of the halogenated allyls include allyl chloride, 2-butenyl bromide, 1-chloro-2-phenyl-2-pentene and the like.

Examples of the allyl alcohols include 2-butenyl alcohol, 2,3-dimethyl-2-butenyl alcohol, 3-bromoallyl alcohol, cinnamyl alcohol, crotyl alcohol, 3-methyl-2-cyclohexene-1-ol, 3-methyl-2-butene-1-ol, geraniol, 2-pentene-1-ol, 3-butene-2-ol, 1-hexene-3-ol, 2-methyl-3-phenyl-2-propene-1-ol, 1-acetoxy-4-hydroxycyclopentene-2,1,2-dihydrocatechol, 3-hexene-2,5-diol, and the like.

Examples of the allylamines include allyldiethylamine, 3-methoxyallyldiphenylamine, triallylamine, 2-butenyldibenzylamine, and the like.

Examples of the allyl sulfones include allyl phenyl sulfone, methylyl-p-tolylsulfone, 2-methyl-3-sulfolene, 1,3-diphenylallylmethylsulfone, and the like.

Example of the allyl sulfonates include allyl toluene-4-sulfonate, 3-thiophenmethanesulfonate, 4-chloro-2-butenyl-methanesulfonate, and the like.

Example of the allyl esters of carboxylic acid include allyl acetate, 2-hexenyl acetate, 2,4-hexadienyl acetate, prenyl acetate, geranyl acetate, farnesyl acetate, cinnamyl acetate, rinaryl acetate, 3-butene-2-yl acetate, 2-cyclopentenyl acetate, 2-trimethylsilylmethyl-2-propenyl acetate, 2-methyl-2-cyclohexenyl acetate, 1-phenyl-1-butene-3-yl propionate, 1-cyclohexyl-2-butene butyrate, 4-cyclopenten-1,3-diol-1-acetate, 1,4-diacetoxy-2-butene, 3-acetoxy-4-hydroxy-1-butene, and the like.

Example of the allyl carbonates include allylmethyl carbonate, 4-acetoxy-2-butenylethyl carbonate, nerylmethyl carbonate and the like.

Examples of the allyl carbamates include allyl-N-(4-fluorophenyl)carbamate, 2-butenyl-N-methyl carbamate, furfuryl-N-(2-methoxydiphenyl)carbamate and the like.

Examples of the allylesters of phosphoric acid include allyldimethyl phosphate, 3-methyl-2-butenyldiphenyl phosphate, methylethylfurfuryl phosphate and the like.

Examples of the allyl ethers include allyl ethyl ether, allyl phenyl ether, 2,3-diphenylallylisopropyl ether, 2-butenyl-4-fluorophenyl ether and the like.

Examples of the phenylethylene oxides include butadiene monoxide, cyclopentadiene monoxide, 1,3-cyclohexadiene monoxide and the like.

Particularly preferable examples of the allyl starting material compound include a mixture of at least two compounds selected from the group consisting of 3,4-disubstituted 1-butene expressed by the following formula (b), 1,4-disubstituted 2-butene expressed by the following formula (c) and their compounds.

$$CH_2=CH-CHR^1-CH_2R^2 \qquad (b)$$

In the above formula (b), $R^1$ and $R^2$ are respectively independently an acetoxy group or a hydroxyl group, at least one of which is an acetoxy group. Examples of the 3,4-disubstituted 1-butene expressed by the above formula (b) include 3,4-diacetoxy-1-butene, 3-acetoxy-4-hydroxy-1-butene, 4-acetoxy-3-hydroxy-1-butene and 3,4-dihydroxy-1-butene.

$$R^3CH_2-CH=CH-CH_2R^4 \qquad (c)$$

In the formula (c), $R^3$ and $R^4$ are respectively independently an acetoxy group or a hydroxyl group, at least one of which is an acetoxy group. Examples of the 1,4-disubstituted 2-butene expressed by the above formula (c) include 1,4-diacetoxy-2-butene, 1-acetoxy-4-hydroxy-2-butene and 1,4-dihydroxy-2-butene.

Next, the nucleophilic agent used in the production method of the present invention is explained hereinafter. Generally, a nucleophilic agent is a reactive material having a non-covalent electron pair, which is basic and has a tendency of attacking a carbon nucleus, but in the present invention, a kind of the nucleophilic agent is not specially limited, and every kind of nucleophilic agent can be used. However, in order to form an allyl compound by nucleophilicly attacking a Π-allyl complex, the nucleophilic agent used in the present invention is preferably an oxygen nucleophilic agent, a carbon nucleophilic agent or a nitrogen nucleophilic agent, wherein a non-covalent electron pair on an oxygen atom, a carbon atom or a nitrogen atom carries out the nucleophilic attacking. Also, in order to improve a reaction rate, under the reaction conditions, it is preferable that the whole amount or a part of the nucleophilic agent is soluble in a solvent, compatible with an allyl starting material or meltable by heating. From this viewpoints, a nucleophilic agent usually having a molecular weight of at most 600 is used.

Examples of the oxygen nucleophilic agent usable in the present invention include a proton adduct compound expressed by $E^1O-H$ containing a nucleophilic oxygen atom, an anion expressed by $E^1O^-$ which is a deprotonated material, or a compound which can be an anion in the reaction system. In the above formula, $E^1$ is a hydrogen atom or an organic group. The organic group is a material having a carbon atom, a nitrogen atom, a phosphorus atom or a sulfur atom bonded to the nucleophilic oxygen atom, which becomes a liquid in the reaction system and does not adversely affect the reaction system.

When $E^1$ is an organic group, the carbon number of the organic group is preferably in a range of from 1 to 30 so that it can be easily soluble in the reaction system. The carbon number is more preferably from 1 to 20, most preferably from 1 to 10. Also, the molecular weight of the oxygen nucleophilic agent is preferably at most 400, more preferably at most 300, most preferably at most 200.

Examples of the organic group bonded to the nucleophilic oxygen atom by way of a carbon atom include an unsubstituted or substituted chain-like or cyclic alkyl group, an unsubstituted or substituted aryl group, and the like. Examples of the organic group bonded to the nucleophilic oxygen atom by way of a nitrogen atom include an unsubstituted or substituted amino group or a group having a C=N bond.

Examples of the organic group bonded to the nucleophilic oxygen atom by way of a phosphorus atom include an unsubstituted or substituted phosphonate group, an unsubstituted or substituted phosphinate group or an unsubstituted or substituted phosphinoyl group.

Examples of the organic group bonded to the nucleophilic oxygen atom by way of a sulfur atom include an unsubstituted or substituted sulfonyl group.

Substituents of the above illustrated groups are not specially limited so long as they are an organic group and do not adversely affect the reaction system, and preferable examples include a chain-like or cyclic alkyl group, an aryl group, an alkoxy group, an arylalkoxy group, an aryloxy group, an alkylaryloxy group, an alkylthio group, an arylthio group, an acyl group or an acyloxy group. When the above illustrated groups have these substituents, the total carbon number including substituents should be within the above-mentioned range.

However, even when an oxygen nucleophilic agent is within the above-mentioned definition, it is necessary to exclude such an oxygen nucleophilic agent as to be the same as substituent (X or its anion $X^-$ in the above formula (a)) or its proton adduct (X—H), which is eliminated from an allyl starting material compound depending on the reaction, since it provides such a state as not proceeding the reaction apparently or such a state as producing an isomerized material of the allyl starting material compound as a product, which has the same compositional formula as the allyl starting material but has a different structure.

Examples of an oxygen nucleophilic agent in a proton adduct form are illustrated below. When $E^1$ is a hydrogen atom, it is water.

When $E^1$ is an organic group wherein a nucleophilic oxygen and a carbon atom are bonded to each other, their examples include hydroxy compounds, carboxylic acids, thiocarboxylic acids or selenocarboxylic acids.

Examples of the hydroxy compounds include alcohols such as methanol, ethanol, n-propanol, n-butanol, sec-butanol, t-butanol, allyl alcohol, 2-ethylhexyl alcohol, 4-chloro-1-butanol, benzyl alcohol, cyclohexanol, ethylene glycol, 1,3-propanediol and 1,4-butanediol; and phenols such as phenol, p-methoxyphenol, 2,4-dimethylphenol, 1-naphthol, 2-naphthol, 3,6-di-t-butyl-2-naphthol, 2-pyridinol or 2-bromo-4-pyridinol.

Examples of the carboxylic acids include aliphatic carboxylic acids such as acetic acid, propionic acid, butyric acid, chloroacetic acid, oxalic acid or adipic acid; and aromatic carboxylic acids such as benzoic acid, naphthalene-2-carboxylic acid, m-cyanobenzoic acid or o-toluic acid.

Examples of the thiocarboxylic acids include a compound expressed by $CH_3C(=S)-OH$ or a compound expressed by $PhC(=S)-OH$.

Examples of the selenocarboxylic acids include a compound expressed by $CH_3C(=Se)-OH$ or a compound expressed by $PhC(=Se)-OH$. In the present specification, Ph means a phenyl group.

When $E^1$ is an organic group wherein a nucleophilic oxygen and a nitrogen atom are bonded to each other, its examples include hydroxyamines such as N,N-diethylhydroxyamine, N,N-dibenzylhydroxyamine or the like; oximes such as acetone oxime, benzophenone oxime, cyclopentanone oxime or the like; carbamates such as t-butyl-N-hydroxy carbamate, and imides such as N-hydroxymaleimide, N-hydroxy succinimide, or 1-hydroxybenzotriazole, and the like.

When $E^1$ is an organic group wherein a nucleophilic oxygen and a phosphorus atom are bonded to each other, its examples include phosphinic acids, phosphonic acid esters, phosphoric acid esters, and the like.

Examples of the phosphinic acids include dimethylphosphinic acid, diphenylphosphinic acid or the like; examples of the phosphonic acid esters include ethyl phosphonic acid, propyl phosphonic acid monophenyl ester or the like; and examples of the phosphoric acid esters include diphenyl phosphate, dimethyl phosphate or the like.

When $E^1$ is an organic group wherein a nucleophilic oxygen and a sulfur atom are bonded to each other, its examples include sulfonic acids such as p-toluenesulfonic acid, methanesulfonic acid, ethanesulfonic acid or the like; and sulfuric acid monoesters such as sulfuric acid monophenylester, sulfuric acid monooctylester or the like.

All of the above illustrated examples are shown in a proton adduct form, but each of the above illustrated compounds includes a deprotonated product or a compound convertible to its deprotonated product in the reaction system. Examples of the compound convertible to its deprotonated product in the reaction system include a compound in which the deprotonated product is bonded to other atom or atom group. Examples of the other atom or atom group bonded to the deprotonated product include various kinds of monovalent cations (such as $Na^+$, $K^+$ or the like).

Among the above illustrated examples, the compound wherein $E^1$ is an organic group having a nucleophilic oxygen and a carbon atom bonded to each other is particularly preferable, and the following types (i) to (iv) oxygen nucleophilic agents are particularly preferable.

(i) Alcohols expressed by RO—H or RO$^-$ (wherein R is an alkyl group which may have a substituent and may have a double bond or a triple bond in a carbon chain) or their deprotonated products.

(ii) Hydroxy aryls expressed by ArO—H or ArO$^-$ (wherein Ar is an aryl group which may have a substituent and may contain a hetero atom such as nitrogen, oxygen, phosphorus or sulfur) or their deprotonated products.

(iii) Aliphatic carboxylic acids expressed by R'COO—H or R'COO$^-$ (wherein R' is a hydrogen atom or an alkyl group which may have a substituent and may have a double bond or a triple bond in a carbon chain).

(iv) Aromatic carboxylic acids expressed by Ar'COO—H or Ar'COO$^-$ (wherein Ar' is an aryl group which may have a substituent and may have a hetero atom such as nitrogen, oxygen, phosphorus or sulfur) or their deprotonated products.

Examples of the type (i) oxygen nucleophilic agent include a saturated or unsaturated alcohol and their substituent-containing products, and a saturated or unsaturated diol, a multi-substituted alcohol or their substituent-containing products.

Examples of the saturated or unsaturated alcohol and their substituent-containing products include methyl alcohol, ethyl alcohol, n-propyl alcohol, i-propyl alcohol, n-butyl alcohol, 2-ethylhexanol, n-octanol, allyl alcohol, crotyl alcohol, benzyl alcohol, 1-bromo-2-propanol, 2-methylcyclopentanol, 2-phenylethanol, neopentyl alcohol, 4-cyclohexenol, or cholesterol. Examples of the saturated or unsaturated diol, the multi-substituted alcohol or their substituent-containing products include 1,2-ethane diol, 1,3-propane diol, 1,4-buthane diol, 2-butene-1,4-diol, 2-chloro-1,3-propane diol, 1,2-cyclopentane diol, glycerin, or pentaerythritol.

Among the type (i) oxygen nucleophilic agents, a saturated alcohol or a saturated diol is preferable, examples of which include a $C_1$–$C_{10}$ alcohol such as methyl alcohol, ethyl alcohol, n-propyl alcohol, i-propyl alcohol, n-butyl alcohol, 2-ethylhexanol, or n-octanol, and a $C_1$–$C_{10}$ diol such as 1,2-ethanediol, 1,3-propane diol or 1,4-butane diol.

Examples of the type (ii) oxygen nucleophilic agents include monohydroxy aryl and their substituent-containing products, and di- or polyhydroxy aryl and their substituent-containing products. Examples of the monohydroxy aryl and their substituent-containing products include phenol, cresol, 4-nitrophenol, 2-fluorophenol, 2,4-di-t-butylphenol, 2,4-di-t-butyl-6-methylphenol, 1-naphthol, 2-naphthol, or 3-t-butyl-2-naphthol. Examples of the di- or polyhydroxy aryl and their substituent-containing products include catechol, resorcinol, hydroquinone, 2,4-dihydroxyphenyl ethyl ketone, 4-n-hexyl resorcinol, 1,8-dihydroxy naphthalene, 1,2-dihydroxy naphthalene, 1-methyl-2,3-dihydroxy naphthalene, or 1,2,4-benzene triol.

Among the type (ii) oxygen nucleophilic agents, monohydroxy aryl or dihydroxy aryl is preferable, examples of which include a $C_1$–$C_{15}$ hydroxy aryl such as phenol, 1-naphthol, 2-naphthol, catechol, resorcinol, hydroquinone or 2,6-dihydroxy naphthalene.

Examples of the type (iii) oxygen nucleophilic agents include a saturated aliphatic carboxylic acid and their substituent-containing products, an unsaturated aliphatic carboxylic acid and their substituent-containing products, and aliphatic dicarboxylic acids and their substituent-containing products, and the like. Examples of the saturated aliphatic carboxylic acid and their substituent-containing products include acetic acid, propionic acid, butyric acid, valeric acid, caproic acid, lauric acid, cyclohexane carboxylic acid, α-methyl butyric acid, γ-chloro-α-methyl valeric acid, α-hydroxy propionic acid, γ-phenyl butyric acid, and the like. Examples of the unsaturated aliphatic carboxylic acid and their substituent-containing products include acrylic acid, oleic acid, linolic acid, linolenic acid, 2-cyclohexene carboxylic acid, 4-methoxy-2-butenoic acid, methacrylic acid, and the like. Examples of the aliphatic dicarboxylic acid and their substituent-containing products include oxalic acid, malonic acid, succinic acid, glutaric acid, adipic acid, maleic acid, fumaric acid, and the like.

Among the type (iii) oxygen nucleophilic agents, a saturated aliphatic carboxylic acid or a saturated aliphatic dicarboxylic acid is preferable, examples of which include a $C_1$–$C_{20}$ aliphatic carboxylic acid such as acetic acid, propionic acid, butyric acid, valeric acid, caproic acid, lauric acid, myristic acid, palmitic acid, stearic acid, oxalic acid, malonic acid, succinic acid, glutaric acid, adipic acid, and the like.

Examples of the type (iv) oxygen nucleophilic agents include an aromatic carboxylic acid and their substituent-containing products, and an aromatic di- or polycarboxylic acid and their substituent-containing products. Examples of the aromatic carboxylic acid and their substituent-containing products include benzoic acid, 3-cyanobenzoic acid, 2-bromobenzoic acid, 2,3-dimethoxybenzoic acid, 4-phenoxybenzoic acid, p-nitrobenzoic acid, m-toluic acid, o-methoxybenzoic acid, phthalic acid monomethyl ester, terephthalic acid monoethyl ester, naphthalene-1-carboxylic acid, 1-methylnaphthalene-2-carboxylic acid, 2-ethoxynaphthalene-1-carboxylic acid, 1-hydroxynaphthalene-2-carboxylic acid, 1-bromonaphthalene-2-carboxylic acid, anthracene-9-carboxylic acid, phenanthrene-4-carboxylic acid, picolinic acid, nicotinic acid, isonicotinic acid, 2-methoxythionicotinic acid, 6-chloronicotinic acid, isoquinoline-1-carboxylic acid, quinoline-3-carboxylic acid, quinoline-4-carboxylic acid, 4-methoxyquinoline-2-carboxylic acid, and the like. Examples of the aromatic di- or polycarboxylic acid and their substituent-containing products include phthalic acid, isophthalic acid, terephthalic acid, benzene-1,2,4-tricarboxylic acid, benzene-1,2,4,5-tetracarboxylic acid, naphthalene-1,4-dicarboxylic acid, naphthalene-1,8-dicarboxylic acid, naphthalene-2,3-dicarboxylic acid, naphthalene-2,6-dicarboxylic acid, naphthalene-1,4,5,8-tetracarboxylic acid, and the like.

Among the type (iv) oxygen nucleophilic agents, an aromatic carboxylic acid or dicarboxylic acid is preferable, examples of which include a $C_6$–$C_{15}$ aromatic carboxylic acid such as benzoic acid, naphthalene-2,6-dicarboxylic acid, phthalic acid, isophthalic acid or terephthalic acid.

Preferable examples of a carbon nucleophilic agent include carboanions expressed by $E^2E^3E^4C^-$ or its proton adducts expressed by $E^2E^3E^4CH$. In the above formulae, $E^2$ to $E^4$ are respectively independently a hydrogen atom, a halogen atom, a hydroxyl group, a cyano group, a nitro group, a sulfonyl group, a carboxyl group or a chain-like or cyclic alkyl group, an aryl group, an acyl group, a carbamoyl group, an alkoxycarbonyl group, an aryloxy carbonyl group, an acyloxy group, an alkoxy group, an aryloxy group, an alkylthio group, an arylthio group, an isocyano group, an alkylidene amino group or a dialkoxyphospholyl group. The above illustrated groups may further have a substituent. The substituent is an organic group and is not specially limited so long as it does not adversely affect the reaction system, but preferable examples include a chain-like or cyclic alkyl group, an aryl group, an alkoxy group, an aryloxy group, an alkylthio group, an arylthio group, an acyl group or an acyloxy group.

When the above substituents illustrated as $E^2$ to $E^4$ and their dependent substituents are a group containing a carbon chain, the carbon chain may have at least one carbon-carbon double bond or triple bond. Further, at least two optional groups among $E^2$ to $E^4$ may be bonded to each other to form at least one cyclic structure. Still further, it is necessary that at least one of $E^2$ to $E^4$ is an electron withdrawing group. Among them, it is more preferable that at least two of $E^2$ to $E^4$ are electron withdrawing groups.

A carbon number of a carbon nucleophilic agent is usually from 1 to 50, preferably from 1 to 40, more preferably from 1 to 30. Also, its molecular weight is usually at most 600, preferably at most 500, more preferably at most 400.

Among the above carbon nucleophilic agents, carboanions are formed from compounds having no such a charge as having a substituent such as a proton bonded to a non-covalent electron pair, but such an original compound as it is may be used for reaction or may be converted to a carboanion state by withdrawing a proton to be used for reaction. In the latter case, when an alkali metal ion is used as a counter cation to the carboanion, it is generally possible to carry out the reaction at a higher reaction activity. Usually, the carbon nucleophilic agent takes a nucleophilic carboanion structure only when withdrawing a proton from its original compound, and it is therefore preferable that the original compound is a compound (proton adduct) having an active proton, i.e. an acidic proton.

Preferable examples of the carbon nucleophilic agent in a hydrogen adduct form include malonic acid ester derivatives such as diethyl malonate or diethyl methylmalonate; α-substituted acetic acid ester derivatives such as ethyl α-bromopropionate, ethyl acetoacetate, methyl cyanoacetate, benzyl isocyanoacetate, ethyl phenylsulfonylacetate, butyl nitroacetate or t-butyl phenylthioisocyanoacetate; substituted nitromethane derivatives such as nitroethane or dinitromethane; diacylmethane derivatives such as heptane-3,5-dione or pentane-2,4-dione; sulfonyl methane derivatives such as dimethylsulfonylmethane or phenylsulfonyl allyl; substituted acetonitriles such as phenyl acetonitrile or phenoxyphenylthio acetonitrile; alkylidene aminomethane derivatives such as diethyl cyclohexylideneaminomethylphosphonate or bis(2-propylidene amino)methane; or fluorene, and the like.

More preferable examples of the carbon nucleophilic agent include compounds wherein at least one of $E^2$ to $E^4$ is an alkoxycarbonyl group. Examples of these compounds include diethyl malonate, ethyl acetoacetate or methyl cyanoacetate. Among them, compounds wherein at least two of $E^2$ to $E^4$ are alkoxycarbonyl groups are particularly preferable. Examples of these compounds include diethyl malonate.

Preferable examples of a nitrogen nucleophilic agent include such amines having at least one hydrogen atom bonded as expressed by $HNE^5E^6$. In the above formula, $E^5$ or $E^6$ is respectively independently a hydrogen atom, a halogen atom, a hydroxyl group, a cyano group, a nitro group, a sulfonyl group, a carboxyl group, a chain-like or cyclic alkyl group, an aryl group, an acyl group, a carbamoyl group, a carbonyl group, an acyloxy group, an alkoxy group or an aryloxy group. The above illustrated groups may further have a substituent. The substituent is not specially limited so long as it is an organic group and does not adversely affect the reaction system, but preferable examples include a chain-like or cyclic alkyl group, an aryl group, an alkoxy group, an aryloxy group, an alkylthio group, an arylthio group, an acyl group or an acyloxy group.

When the above illustrated substituents as $E^5$ and $E^6$ and their dependent substituents are a group having a carbon chain, the carbon chain may have at least one carbon-carbon double bond or triple bond. Also, $E^5$ and $E^6$ may be bonded to each other to form at least one cyclic structure.

The nitrogen nucleophilic agent has a carbon number of preferably 1 to 40, more preferably 1 to 30, most preferably 1 to 20. Also, its molecular weight is preferably at most 500, more preferably at most 400, most preferably at most 300.

In a case of reaction with amines, a non-covalent electron pair on a nitrogen atom of an amine nucleophilicly attacks a terminal allyl carbon of a Π-allyl complex to provide an ammonium cation state as an intermediate, and a proton is withdrawn therefrom to form allylamines neutral in respect of a charge. Therefore, it is necessary that amines should have at least one hydrogen atom bonded. However, in order to further enhance a nucleophilic property of amines, a proton may be previously withdrawn by chemical treatment or the like for providing anionized amines as expressed by $E^5E^6N^-$ to be used for reaction. In such a case, an alkali metal ion is illustrated as a counter cation for the anionized amines.

Preferable examples of the nitrogen nucleophilic agent in a hydrogen adduct form include ammonia; a primary amine such as ethylamine, n-butylamine, i-propylamine, 3-chloro-n-propyl amine, t-butylamine, n-octylamine, allylamine, cyclohexylamine, benzylamine, phenylamine or phenoxyamine; a secondary amine such as dimethylamine, diethylamine, di-i-propylamine, di-n-pentylamine, di-n-undecylamine, di(2-butenyl)amine, dicyclohexylamine, diphenylamine, diphenoxyamine, di(4-bromocyclohexyl)amine, methylethyl amine, t-butyl-n-butylamine, methylphenyl amine, 4-cyano-n-decylneopentylamine, 2-ethoxyethyl-t-butyl amine, N-chloro-N-phenylamine, N-ethoxy-N-ethylamine, N-n-octyl-N-hydroxyamine or N-3,5-dimethylhexyl-N-2-ethylhexylamine; N-substituted or unsubstituted amide compounds such as caproamide, 3-bromobenzamide, ethoxycarbonylamine, N-bromoacetamide, 4-fluoroacetanilide, cyclohexyldi-i-propylaminocarbonylamine, methoxycarbonylpropylamine, carboxylglycine or phenoxycarbonylphenylamine; heterocyclic cyclic amines such as pyrrole, imidazole, pyrrolidine, indole, 2,5-dimethyl pyrrolidine, morpholine or 4-chloro-2,5-dihydroquinoline; or diamines or polyamines such as tetramethylenediamine, N,N'-diethylethylenediamine, hexamethylenediamine or 1,3,5-triaminobenzene.

More preferable examples of the nitrogen nucleophilic agent include a primary amine or a secondary amine wherein at least one of $E^5$ and $E^6$ is an unsubstituted or substituted alkyl group. Among them, particularly preferable examples include secondary amines wherein both E5 and E6 are an unsubstituted or substituted alkyl group. Particularly preferable examples of the nitrogen nucleophilic agent include dimethylamine, diethylamine, di-i-propylamine, di-n-pentylamine, di-n-undecylamine, di(2-butenyl)amine, dicyclohexylamine, di(4-bromocyclohexyl)amine, methylethylamine, t-butyl-n-butylamine, 4-cyano-n-decylneopentylamine, 2-ethoxyethyl-t-butylamine, N-3,5-dimethylhexyl-N-2-ethylhexylamine and the like.

Hereinafter, a catalyst used in the production method of the present invention is explained in details. The catalyst used in the present invention contains at least one transition metal compound and a bidentate coordinated phosphite compound having a specific structure.

The transition metal compound used in the present invention is at least one kind of compound containing a transition metal selected from the group consisting of transition metals belonging to Group 8 to Group 10 of the Periodic Table (according to IUPAC Inorganic Chemistry Nomenclature, Revised Edition, 1998). Examples of the transition metal compound include an iron compound, a ruthenium compound, an osmium compound, a cobalt compound, a rhodium compound, an iridium compound, a nickel compound, a palladium compound and a platinum compound, and among them, a ruthenium compound, a rhodium compound, an iridium compound, a nickel compound, a palladium compound and a platinum compound are preferable, and a nickel compound, a palladium compound and a platinum compound are more preferable, and a palladium compound is particularly preferable. Kinds of these compounds are optional, examples of which include compounds of the above-mentioned transition metals such as an acetyl acetonate compound, a halide, a sulfate, a nitrate, an organic salt, an inorganic salt, an alkene-coordinated compound, an amine-coordinated compound, a pyridine-coordinated compound, a carbon monoxide-coordinated compound, a phosphine-coordinated compound, a phosphite-coordinated compound or the like.

Examples of the above transition metal compounds are illustrated below. Examples of the iron compound include $Fe(OAc)_2$, $Fe(acac)_3$, $FeCl_2$, $Fe(NO_3)_3$ or the like. Examples of the ruthenium compound include $RuCl_3$, $Ru(OAc)_3$, $Ru(acac)_3$, $RuCl_2(PPh_3)_3$ or the like. Examples of the osmium compound include $OsCl_3$, $Os(OAc)_3$ or the like. Examples of the cobalt compound include $Co(OAc)_2$, $Co(acac)_2$, $CoBr_2$, $Co(NO_3)_2$ or the like. Examples of the rhodium compound include $RhCl_3$, $Rh(OAc)_3$, $[Rh(OAc)_2]_2$, $Rh(acac)(CO)_2$, $[Rh(OAc)(cod)]_2$, $[RhCl(cod)]_2$ or the like. Examples of the iridium compound include $IrCl_3$, $Ir(OAc)_3$, $[IrCl(cod)]_2$ or the like. Examples of the nickel compound include $NiCl_2$, $NiBr_2$, $Ni(NO_3)_2$, $NiSO_4$, $Ni(cod)_2$, $NiCl_2(PPh_3)_3$ or the like. Examples of the palladium compound include $Pd(0)$, $PdCl_2$, $PdBr_2$, $PdCl_2(cod)$, $PdCl_2(PPh_3)_2$, $Pd(PPh_3)_4$, $Pd_2(dba)_3$, $K_2PdCl_4$, $K_2PdCl_6$, $PdCl_2(PhCN)_2$, $PdCl_2(CH_3CN)_2$, $Pd(dba)_2$, $Pd(NO_3)_2$, $Pd(OAc)_2$, $Pd(CF_3COO)_2$, $PdSO_4$, $Pd(acac)_2$, other carboxylate compounds, an olefin-containing compound, an organic phosphine-containing compound such as $Pd(PPh_3)_4$, allyl palladium chloride dimer, or the like. Examples of the platinum compound include $Pt(acac)_2$, $PtCl_2(cod)$, $PtCl_2(CH_3CN)_2$, $PtCl_2(PhCN)_2$, $Pt(PPh_3)_4$, $K_2PtCl_4$, $Na_2PtCl_6$, $H_2PtCl_6$ or the like. In the above illustrations, "cod" means "1,5-cyclooctadiene", "dba" means "dibenzylideneacetone", "acac" means "acetylacetonate", and "Ac" means "acetyl group".

Kinds of the transition metal compounds are not specially limited, and may be a monomer, a dimer and/or a polymer so long as they are an active metal complex.

An amount of the transition metal compound used in the present invention is not specially limited, but in view of a catalytic activity and economic conditions, it is preferable to use the transition metal compound in an amount of generally at least $1 \times 10^{-8}$ (0.01 mol ppm) mol equivalent, preferably at least $1 \times 10^{-7}$ (0.1 mol ppm) mol equivalent, more preferably at least $1 \times 10^{-6}$ (1 mol ppm) mol equivalent, and generally at most 1 mol equivalent, preferably at most 0.001 mol equivalent, more preferably at most 0.0001 mol equivalent, to the amount of an allyl compound used as a reaction starting material.

As a bidentate coordinated phosphite compound having a specific structure, a phosphite compound having a structure as expressed by the following formula (I), (II) or (III) is used. Its kind is not specially limited so long as it is a phosphite compound forming a chelating ligand to the above-mentioned transition metal compound. In order to increase catalyst activity, it is preferable to be solved in the reaction system, and its molecular weight is usually at most 3,000, preferably at most 1,500 and usually at least 250, preferably at least 300, more preferably at least 400.

One of the essential features of the present invention resides in that $A^1$ to $A^3$ in the above formulae (I) to (III) have specific structures. The presence of such specific structures provides a catalyst having a high catalyst activity and a high catalyst stability to be used in the present invention.

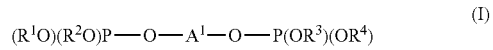
(I)

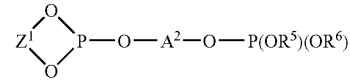
(II)

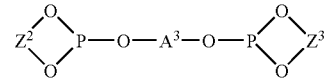
(III)

In the above formulae (I) to (III), $A^1$ to $A^3$ are respectively independently a diarylene group having a branched alkyl group at the ortho-position. The arylene group may further have a substituent so long as it does not adversely affect the reaction system.

$R^1$ to $R^6$ are respectively independently an alkyl group which may have a substituent or an aryl group which may have a substituent (including a heterocyclic compound forming an aromatic 6Π electron cloud on the upper and lower sides of the ring, hereinafter the same). $Z^1$ to $Z^3$ are respectively independently an alkylene group which may have a substituent, an arylene group which may have a substituent, an alkylene-arylene group which may have a substituent, or a diarylene group which may have a substituent.

Each carbon number of $A^1$ to $A^3$ is usually from 1, preferably from 18 to 60, preferably at most 50, more preferably at most 40.

The diarylene group is a group wherein two arylene groups are bonded to each other directly or by way of a bivalent organic group, and is a group having a structure expressed by —Ar$^1$—(Q$^1$)$_n$—Ar$^2$—. Ar$^1$ and Ar$^2$ are respectively independently an arylene group which may have a substituent. Q$^1$ is a bivalent organic group. Its examples include —O—, —S—, —CO— or —CR$^{18}$R$^{19}$—. R$^{18}$ and R$^{19}$ are respectively independently a hydrogen atom, an alkyl group which may have a substituent or an aryl group which may have a substituent. n is 0 or 1. Preferable examples of a substituent which may be contained in the arylene group of Ar$^1$ and Ar$^2$ and the alkyl group and the aryl group of R$^{18}$ and R$^{19}$, include a hydroxyl group, a halogen atom, a cyano group, a nitro group, a formyl group, an alkyl group, an alkoxy group, an aryl group, an aryloxy group, an amino group, an amide group, a perfluoroalkyl group, a trialkylsilyl group, an ester group and the like.

The branched alkyl group at the ortho-position has a carbon number of usually from 3 to 10, preferably from 3 to 7. Examples of the branched alkyl group include preferably a secondary or tertiary alkyl group having a branched chain on the carbon atom bonded to an aromatic ring, and a tertiary alkyl group is particularly preferable.

Examples of such a diarylene group include a group having a structure as expressed by the following formulae (A-1) to (A-19).

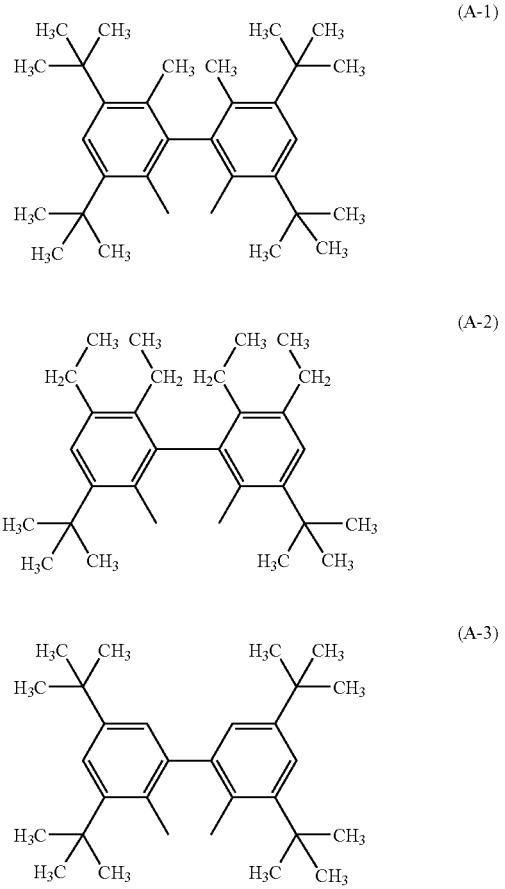

-continued

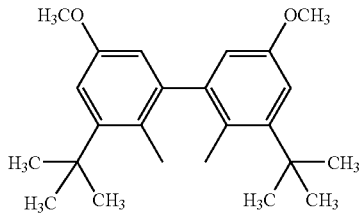
(A-4)

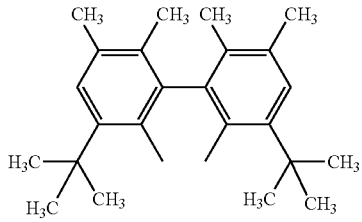
(A-5)

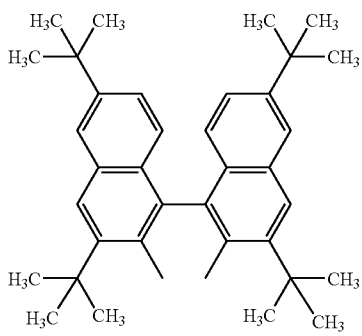
(A-6)

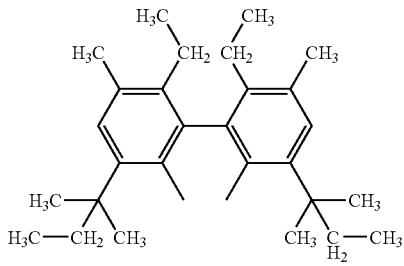
(A-7)

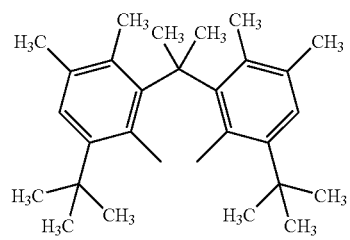
(A-8)

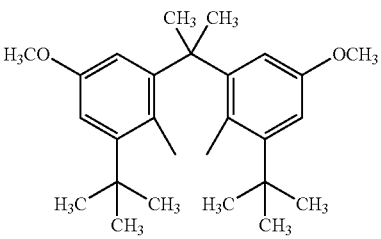
(A-9)

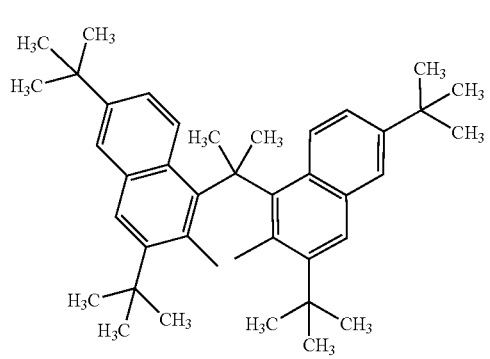
(A-10)
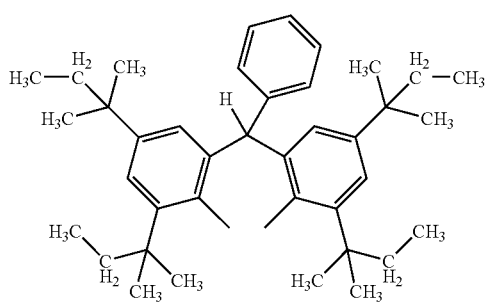
(A-11)
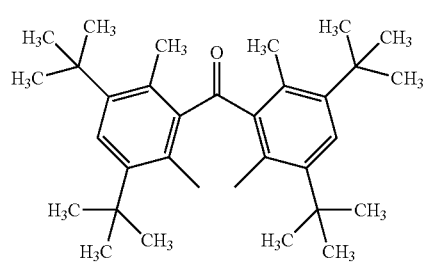
(A-12)
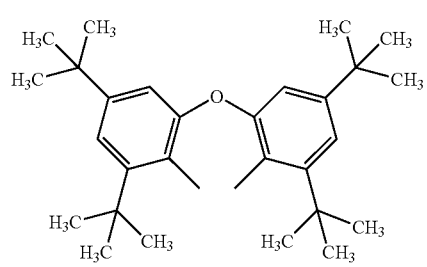
(A-13)
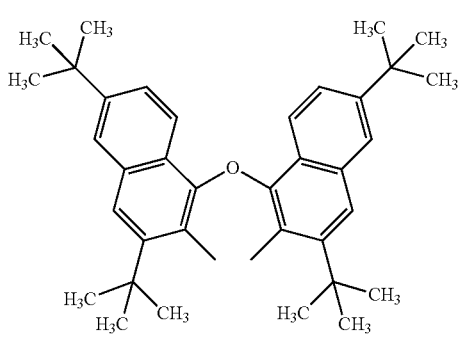
(A-14)
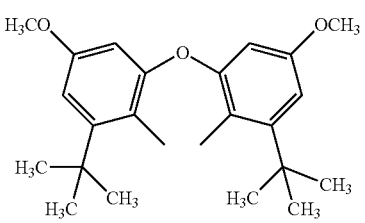
(A-15)
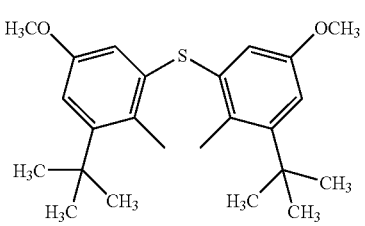
(A-16)
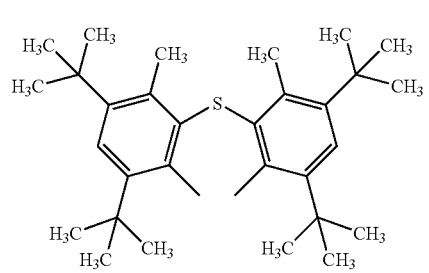
(A-17)
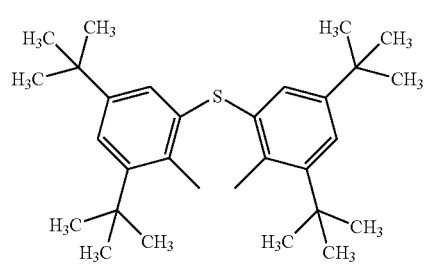
(A-18)
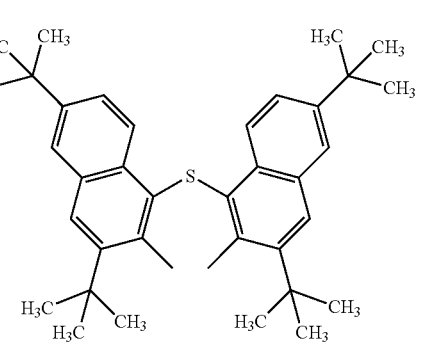
(A-19)
When considering a catalyst activity or a stability of a phosphite ligand, a diarylene group having a structure as expressed by the following formula (IV) or (V) is particularly preferable.

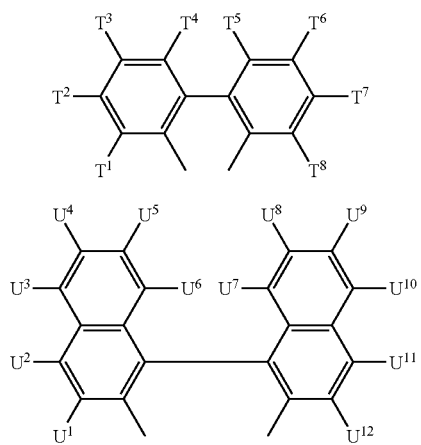

In the above formulae (IV) and (V), $T^1$, $T^8$, $U^1$ and $U^{12}$ are a branched alkyl group, $T^2$ to $T^7$ and $U^2$ to $U^{11}$ are respectively independently a hydrogen atom, a halogen atom, a hydroxy group, a chain-like or cyclic alkyl group, an aryl group, an alkoxy group, an aryloxy group, an ester group, a carboxy group, an amino group, an amide group, an alkylthio group, an acylthio group, an acyl group, or an acyloxy group. These groups may further have a substituent.

The substituent is not specially limited so long as it does not adversely affect the reaction system, but its preferable examples include a halogen atom, a hydroxy group, a chain-like or cyclic alkyl group, an aryl group, an alkoxy group, an aryloxy group, an amino group, an amide group, an alkylthio group, an arylthio group, an acyl group, or an acyloxy group.

$T^1$, T8, $U^1$ and $U^{12}$ have a carbon number of usually from 3 to 10, preferably from 3 to 7. Preferable examples include a secondary or tertiary alkyl group having a branched chain on the carbon atom bonded to an aromatic ring, and a tertiary alkyl group is particularly preferable.

Examples of the branched alkyl group include a secondary alkyl group such as an i-propyl group, an i-butyl group, an i-pentyl group, an i-hexyl group or the like; and a tertiary alkyl group such as a t-butyl group, an amyl group (1,1-dimethylpropyl group), a 1-methyl-1-ethylpropyl group, a 1,1-diethylpropyl group or the like. Among them, a tertiary alkyl group is preferable, and a t-butyl group is most preferable.

$T^2$ to $T^7$ and $U^2$ to $U^{11}$ have a carbon number of usually from 1 to 30, preferably from 1 to 20, more preferably from 1 to 10. Preferable examples of $T^2$ to $T^7$ and $U^2$ to $U^{11}$ include a hydrogen atom, an unsubstituted or substituted alkyl group, an unsubstituted or substituted alkoxy group or an unsubstituted or substituted aryl group.

Particularly preferable groups of $A^1$ to $A^3$, i.e. examples of a group expressed by the above formula (IV) or (V), include groups expressed by the above formulae (A-1) to (A-7).

On the other hand, in the above formulae (I) to (III), $R^1$ to $R^6$ are respectively independently an alkyl group which may have a substituent or an aryl group which may have a substituent (including a heterocyclic compound forming an aromatic 6Π electron cloud on the upper and lower sides of the ring, hereinafter the same).

$R^1$ to $R^6$ have a carbon number of usually from 1 to 40, preferably from 1 to 30, more preferably from 1 to 20. When the above-mentioned alkyl group or aryl group further has a substituent, the total carbon number including the substituent should be within the above-mentioned range.

The substituent is not specially limited so long as it does not adversely affect the reaction system, but preferable examples include a hydroxy group, a halogen atom, a cyano group, a nitro group, a formyl group, an alkyl group, an alkoxy group, an aryl group, an aryloxy group, an amino group, an amide group, a perfluoroalkyl group, a trialkylsilyl group, an ester group, and the like.

Examples of the alkyl group which may have a substituent include a chain-like alkyl group such as a methyl group, an ethyl group, an n-propyl group, an i-propyl group, an n-butyl group, an i-butyl group, a sec-butyl group, a t-butyl group, a hexyl group, an octyl group, or a decyl group; and a cyclic alkyl group such as a cyclopentyl group, a cyclohexyl group or cycloheptyl group.

Examples of the aryl group which may have a substituent include a mono- or dialkylphenyl group such as a phenyl group, a 2-methylphenyl group, a 3-methylphenyl group, a 4-methylphenyl group, a 2-ethylphenyl group, a 2-isopropylphenyl group, a 2-t-butylphenyl group, a 2,3-dimethylphenyl group, a 2,4-dimethylphenyl group, a 2,5-dimethylphenyl group, a 2,6-dimethylphenyl group or a 2,4-di-t-butylphenyl group; a halophenyl group such as a 2-chlorophenyl group, a 3-chlorophenyl group, a 4-chlorophenyl group, a 2,3-dichlorophenyl group, a 2,4-dichlorophenyl group, a 2,5-dichlorophenyl group, a 3,4-dichlorophenyl group, a 3,5-dichlorophenyl group or a pentafluorophenyl group; an alkoxyphenyl group such as a 2-methoxyphenyl group, a 3-methoxyphenyl group, a 4-methoxyphenyl group or 3,5-dimethoxyphenyl group; a cyanophenyl group such as a 4-cyanophenyl group; a nitrophenyl group such as a 4-nitrophenyl group; a haloalkylphenyl group such as a 4-trifluoromethylphenyl group; a mono- or dialkylnaphthyl group such as a 1-naphthyl group, a 2-naphthyl group, a 2-methyl-1-naphthyl group, a 3-t-butyl-2-naphthyl group, or a 3,6-di-t-butyl-2-naphthyl group; a methyloxycarbonylnaphthyl group such as a 3-methyloxycarbonyl-2-naphthyl group; a naphthyl group which may have a substituent, including a hydronaphthyl group such as a 5,6,7,8-tetrahydronaphthalene-2-yl group, or a 5,6,7,8-tetrahydronaphthalene-1-yl group; a nitrogen-containing heterocyclic compound group such as a pyridyl group, a pyrrolyl group, a pyrrazolyl group, an imidazolyl group, a quinolyl group, an isoquinolyl group, or an indolyl group; an oxygen-containing heterocyclic compound group such as a furanyl group; a sulfur-containing heterocyclic compound group such as a thiophenyl group; a heterocyclic compound having at least two hetero atoms on the ring, such as an oxazolyl group, or a thiazolyl group; and the like.

Among the above illustrated groups, when considering a stability of the above-mentioned phosphite, an unsubstituted or substituted aryl group is preferable as $R^1$ to $R^6$, and among the unsubstituted or substituted aryl group, an unsubstituted or substituted phenyl group and an unsubstituted or substituted naphthyl group are particularly preferable.

$Z^1$ to $Z^3$ are respectively independently a bivalent organic group. A kind of the bivalent organic group is not specially limited so long as it does not adversely affect the reaction system, but its preferable examples include a chain-like or cyclic alkylene group, an arylene group, an alkylene-arylene group, or a diarylene group. These organic groups may have a substituent, provided that the substituent does not adversely affect the reaction system. Preferable examples of the substituent include a hydroxyl group, a halogen atom, a cyano group, a nitro group, a formyl group, an alkyl group, an alkoxy group, an aryl group, an aryloxy group, an amino group, an amide group, a perfluoroalkyl group, a trialkylsilyl group and an ester group.

Each carbon number of $Z^1$ to $Z^3$ is usually from 1 to 60. Among them, in case of an unsubstituted or substituted alkylene group, an unsubstituted or substituted arylene group or an unsubstituted or substituted alkylene-arylene group, its carbon number is usually at most 40, preferably at most 30, more preferably at most 20. On the other hand, in case of an unsubstituted or substituted diarylene group, its carbon number is usually at most 60, preferably at most 50, more preferably at most 40.

Examples of the unsubstituted or substituted alkylene group include an ethylene group, a tetramethylethylene group, a 1,3-propylene group, a 2,2-dimethyl-1,3-propylene group, a 1,4-butylene group or the like.

Examples of the unsubstituted or substituted arylene group include a 1,2-phenylene group, a 1,3-phenylene group, a 3,5-di-t-butyl-1,2-phenylene group, a 2,3-naphthylene group, a 1,4-di-t-butyl-2,3-naphthylene group, a 1,8-naphthylene group or the like.

Examples of the unsubstituted or substituted alkylene-arylene group include substituents as expressed by the following structural formulae (D-1) to (D-12).

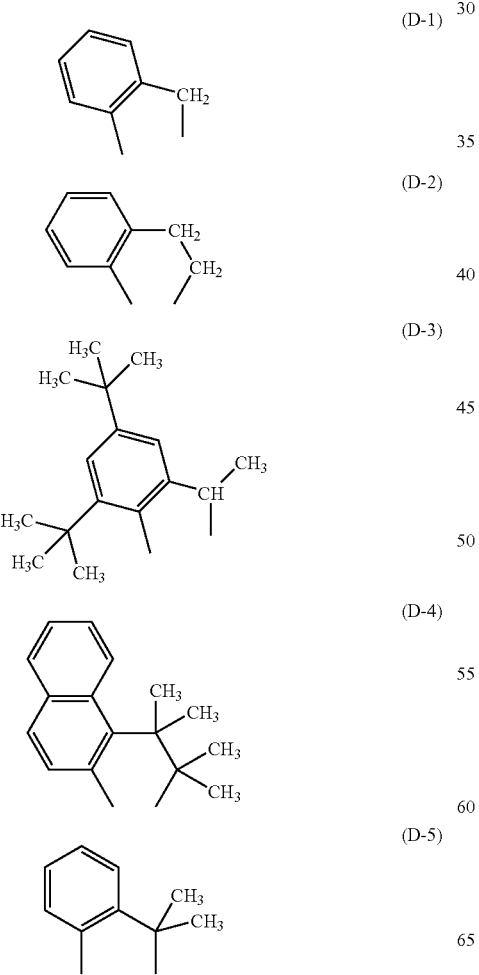

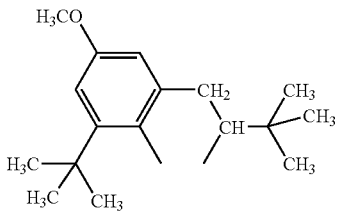

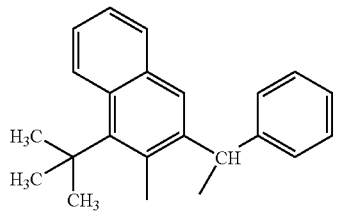

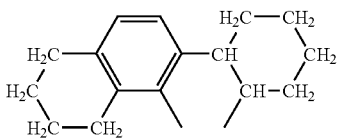

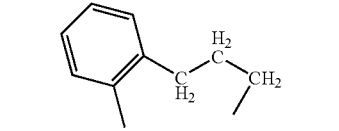

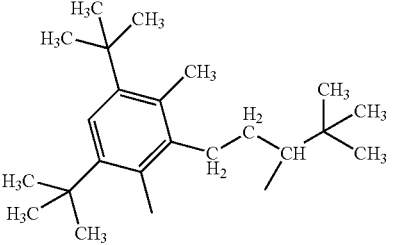

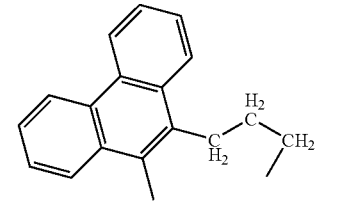

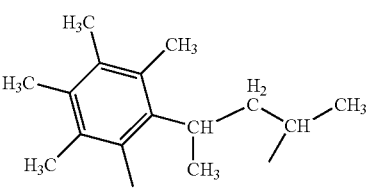

On the other hand, the diarylene group is a group having a structure as expressed by —$Ar^1$—$(Q^1)_n$—$Ar^2$—. The definitions of $Ar^1$ and $Ar^2$, $Q^1$ and n are the same as defined with regard to $A^1$ to $A^3$. Examples of the diarylene group illustrated by the following structural formulae (Z-1) to (Z-48).

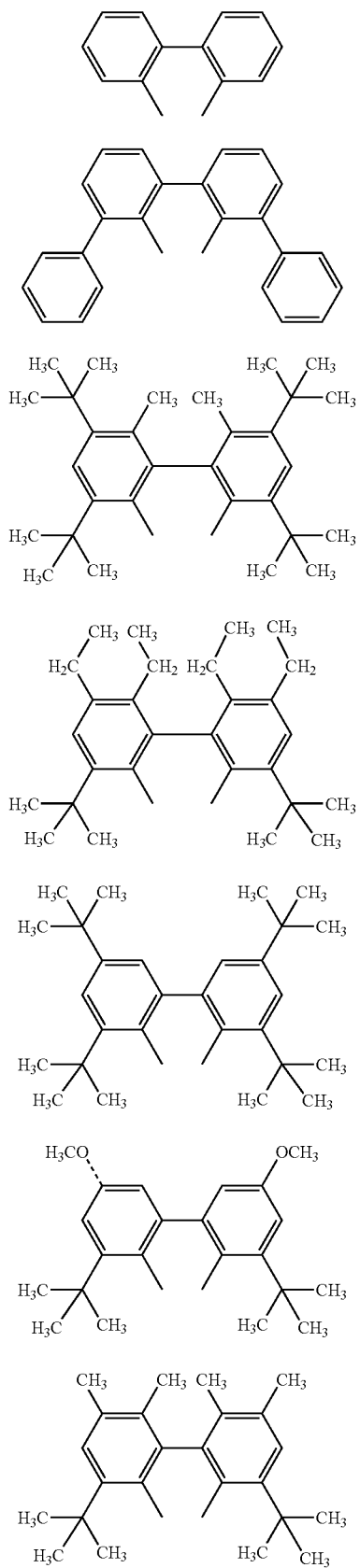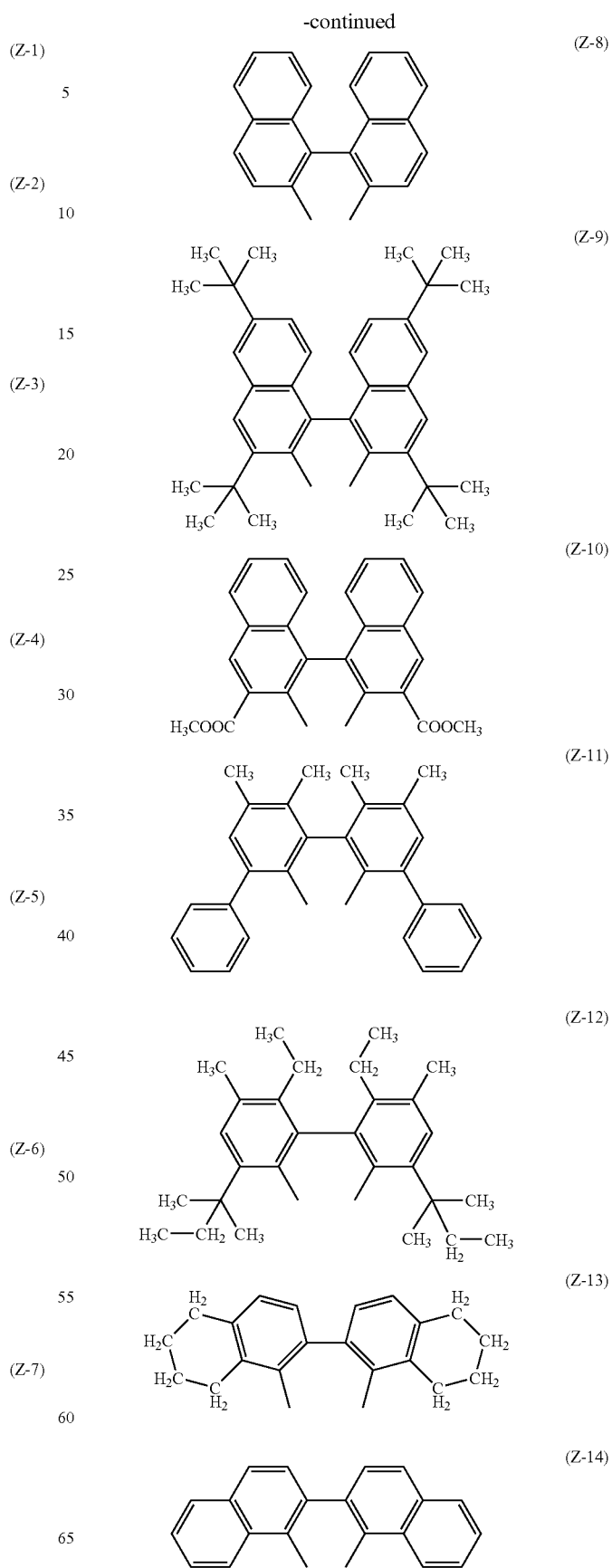

-continued
(Z-15)
(Z-16)
(Z-17)
(Z-18)
(Z-19)
(Z-20)
(Z-21)
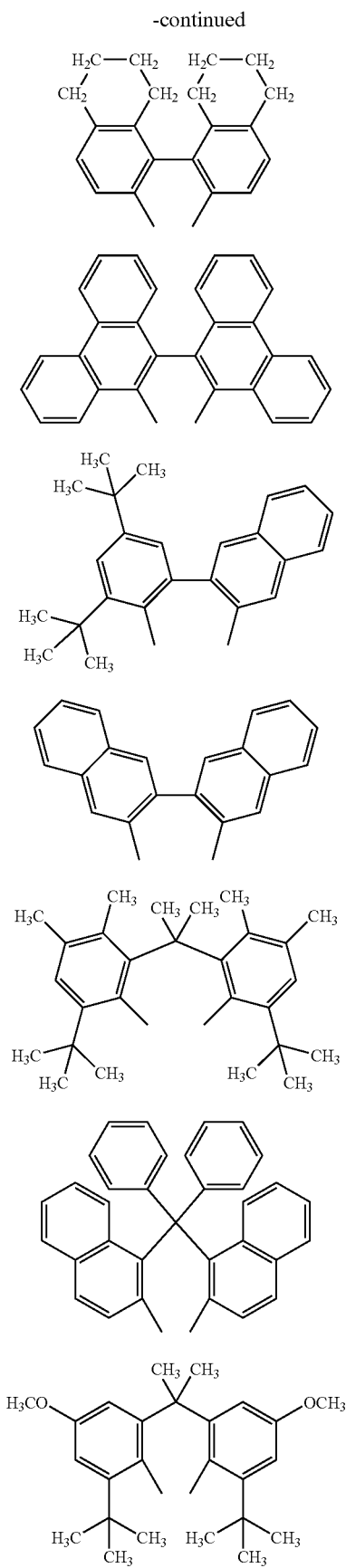
-continued
(Z-22)
(Z-23)
(Z-24)
(Z-25)
(Z-26)
(Z-27)
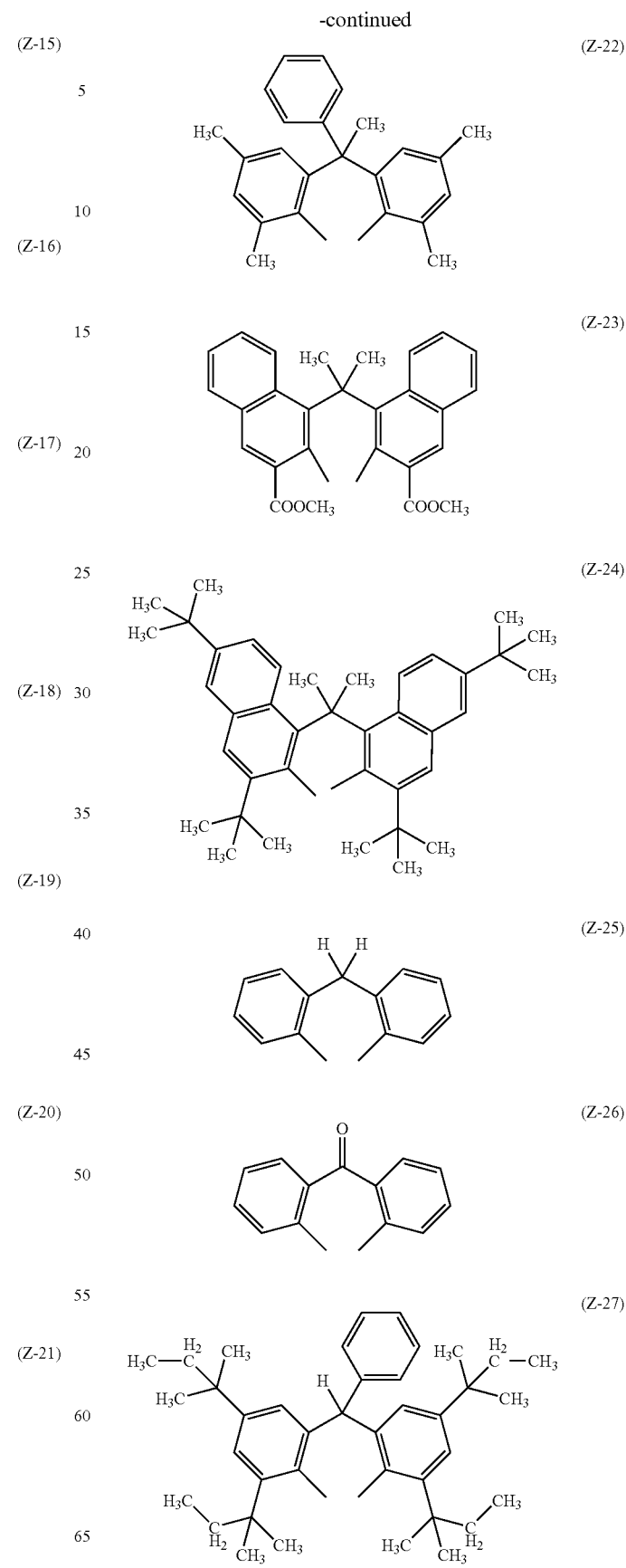

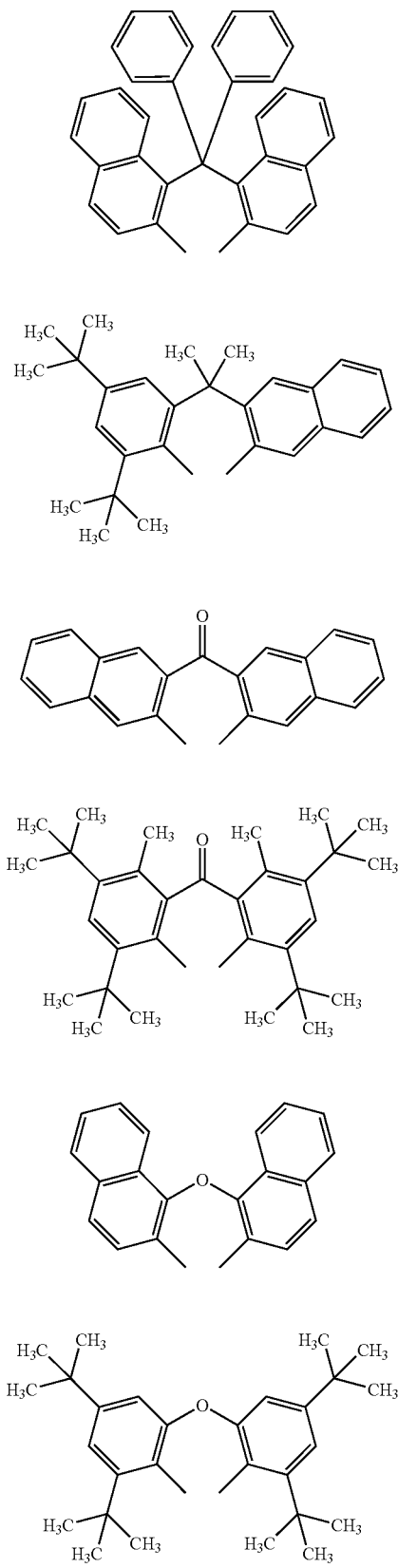

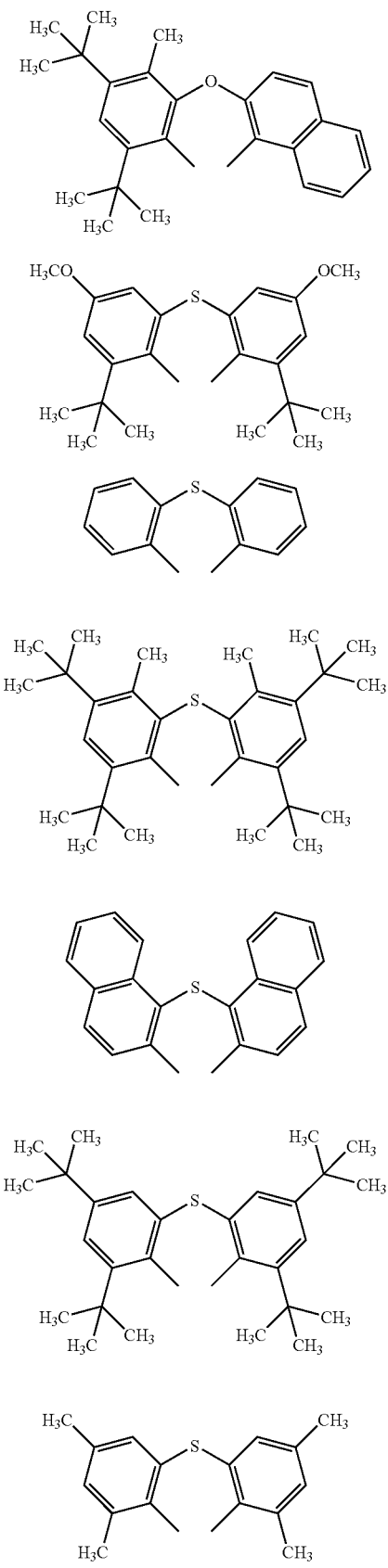

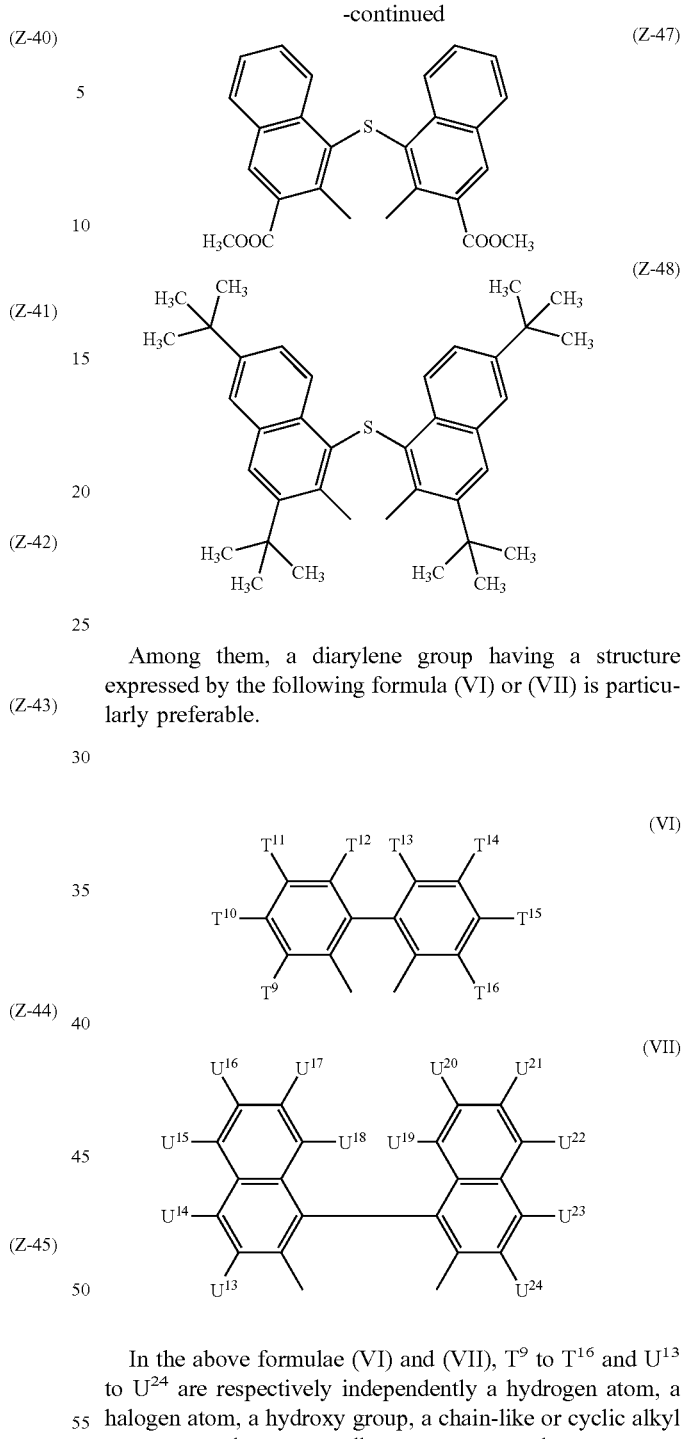

Among them, a diarylene group having a structure expressed by the following formula (VI) or (VII) is particularly preferable.

In the above formulae (VI) and (VII), $T^9$ to $T^{16}$ and $U^{13}$ to $U^{24}$ are respectively independently a hydrogen atom, a halogen atom, a hydroxy group, a chain-like or cyclic alkyl group, an aryl group, an alkoxy group, an aryloxy group, an ester group, a carboxy group, an amino group, an amide group, an alkylthio group, an arylthio group, an acyl group or an acyloxy group. These groups may further have a substituent. The substituent is not specially limited, provided that it does not adversely affect the reaction system, but its preferable examples include a halogen atom, a hydroxy group, a chain-like or cyclic alkyl group, an aryl group, an alkoxy group, an aryloxy group, an amino group, an amide group, an alkylthio group, an arylthio group, an acyl group or an acyloxy group.

The carbon number of $T^9$ to $T^{16}$ and $U^{13}$ to $U^{24}$ is usually from 1 to 30, preferably from 1 to 20, more preferably from 1 to 10. Among the above illustrated groups, more preferable examples of $T^9$ to $T^{16}$ and $U^{13}$ to $U^{24}$ include a hydrogen atom, an unsubstituted or substituted alkyl group, an unsubstituted or substituted alkoxy group or an unsubstituted or substituted aryl group.

Particularly preferable groups of $Z^1$ to $Z^3$, i.e. examples of the group expressed by the above formula (VI) or (VII), include groups expressed by the above formulae (Z-1) to (Z-18).

As mentioned above, by combining substituents constituting phosphite compounds expressed by the above formulae (I) to (III), various phosphites can be provided, preferable examples of which include compounds expressed by the following formulae (L-1) to (L-13).

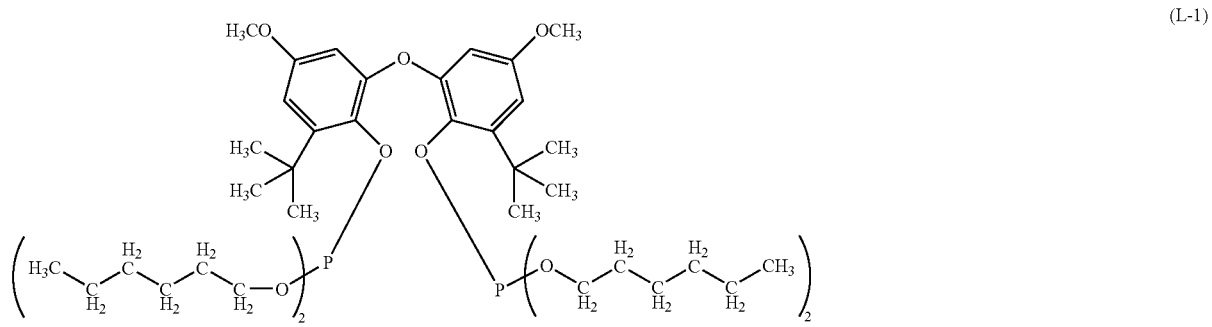

(L-1)

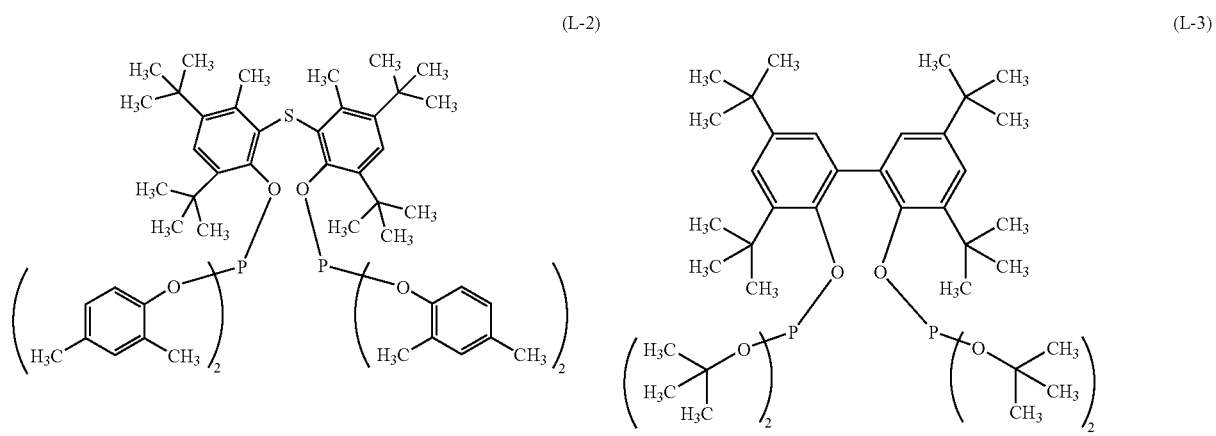

(L-2)

(L-3)

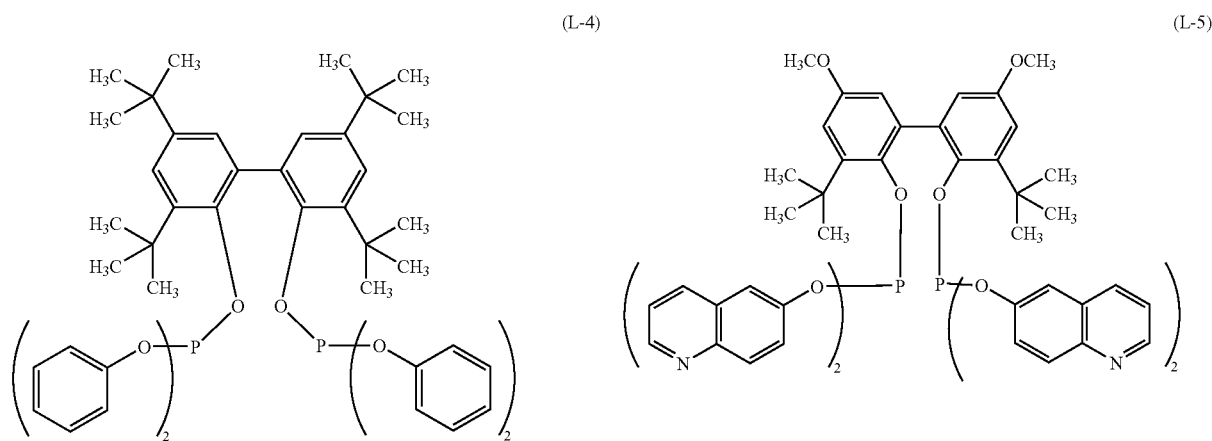

(L-4)

(L-5)

(L-6)
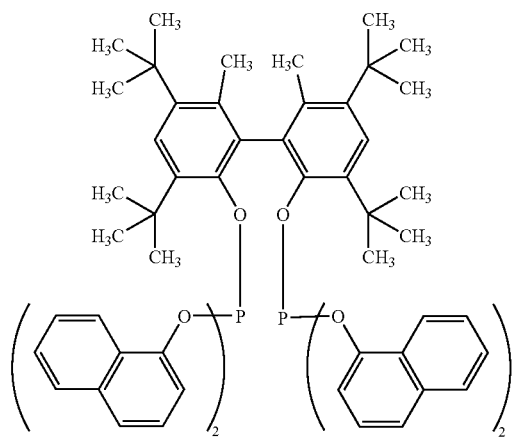
(L-7)
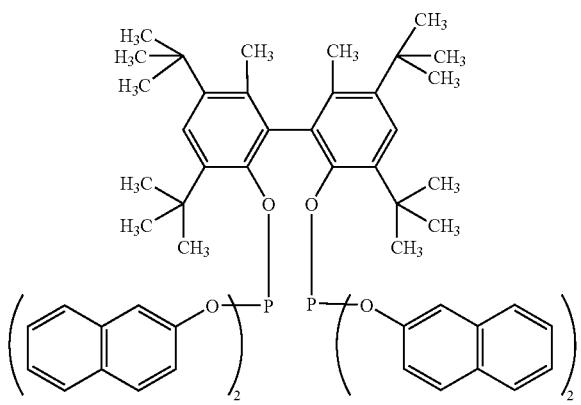
(L-8)
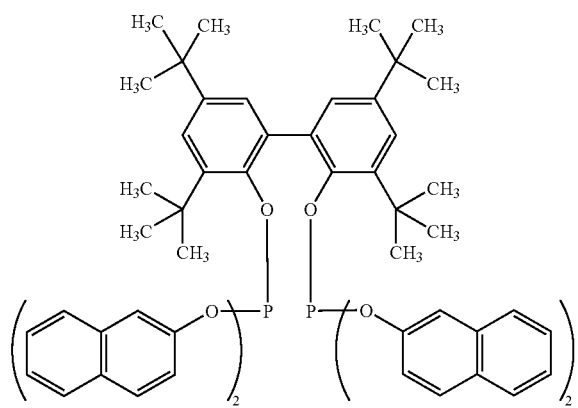
(L-9)
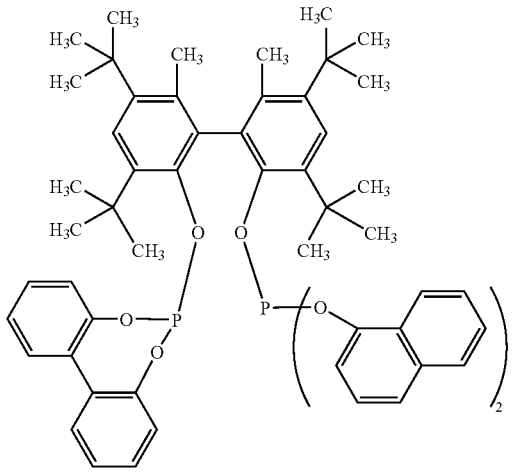
(L-10)
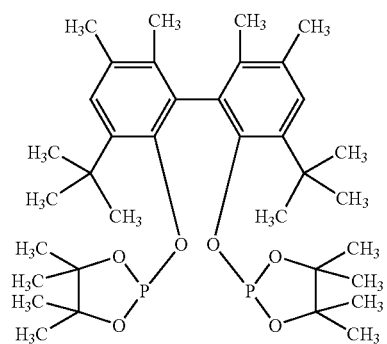
(L-11)
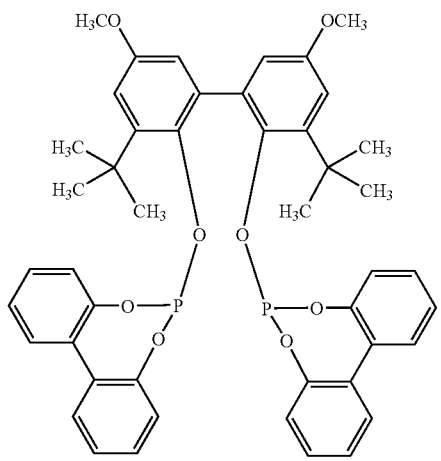

(L-12)

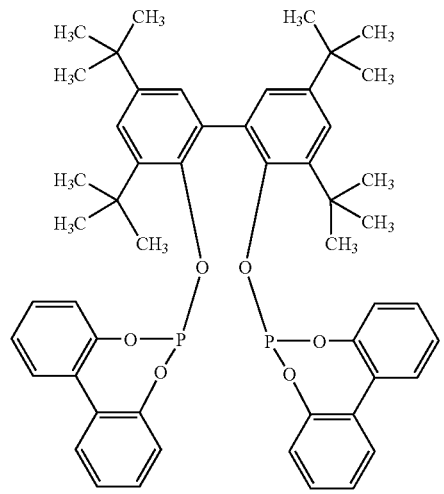

(L-13)

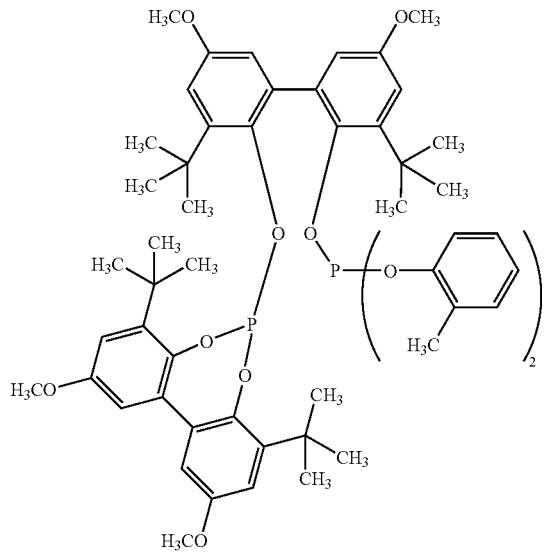

The above bidentate coordinated phosphite compound is used in an amount of a mol ratio of usually at least 0.1, preferably at least 0.5, more preferably at least 1.0, and usually at most 10,000, preferably at most 500, more preferably at most 100, to the above-mentioned transition metal compound.

The above transition metal compound and the bidentate coordinated phosphite compound may be added to the reaction system respectively alone, or may be previously complexed to be used. Alternatively, the above bidentate coordinated phosphite compound may be bonded to some insoluble resin carriers, and the above transition metal compound may be carried thereon to form an insoluble solid catalyst to be used for the reaction. Further, only one kind of the bidentate coordinated phosphite compound may be used for the reaction, or an optional combination of at least two kinds of the bidentate coordinated phosphite compounds may be used at the same time for the reaction.

By reacting an allyl starting material compound and an oxygen nucleophilic agent in the presence of a catalyst comprising the above explained transition metal compound and bidentate coordinated phosphite compound having a specific structure, a new allyl compound (such as ether compounds or ester compounds) can be efficiently produced.

The reaction of the production method of the present invention is usually carried out in liquid phase. The reaction can be carried out either in the presence or absence of a solvent. When using a solvent, any optional solvent is usable so long as it dissolves the catalyst and the starting material compound and does not adversely affect the catalyst activity, and the kind of the solvent is not specially limited. Preferable examples of the solvent include carboxylic acids such as acetic acid, propionic acid or butyric acid, alcohols such as methanol, n-butanol or 2-ethylhexanol, ethers such as diglyme, diphenyl ether, dibenzyl ether, diallyl ether, tetrahydrofuran (THF) or dioxane, amides such as N-methyl-2-pyrrolidone, dimethylformamide or dimethylacetamide, ketones such as cyclohexanone, esters such as butyl acetate, γ-butyrolactone or di(n-octyl) phthalate, aromatic hydrocarbons such as toluene, xylene or dodecylbenzene, aliphatic hydrocarbons such as pentane, hexane, heptane or octane, a high boiling point material formed as a by-product in the allylation reaction system, and an allyl compound as a starting material, an allyl compound as a product, a compound derived from an eliminated group of a starting material allyl compound and the like. An amount of these solvents is not specially limited, but is usually at least 0.1 weight time, preferably at least 0.2 weight time, and usually at most 20 weight times, preferably at most 10 weight times, to a total amount of the allyl compound used as the starting material.

The actual reaction may be carried out by employing various reaction systems. For example, the reaction can be carried out in any of continuous system, semi-continuous system or batch wise system by using a stirring type completely mixing reactor, a plug flow type reactor, a solid bed type reactor, a suspension bed type reactor or the like.

When actually carrying out the reaction, reaction conditions may be optionally selected depending on a reaction substrate or a product. For example, when employing a stirring type completely mixing reactor, the reaction is carried out by a process comprising adding a catalyst solution prepared in a catalyst-preparing tank to a mixture solution of an allyl starting material compound, a nucleophilic agent and an optionally a solvent, introducing the resultant mixture into the reactor continuously or semi-continuously, retaining the reaction mixture at a reaction temperature with stirring to proceed the allylation reaction of the nucleophilic agent, and withdrawing a part of the reaction solution continuously or semi-continuously from the reactor. Also, when employing a plug flow type reactor, the reaction is carried out by passing the reaction solution containing the above starting materials and the catalyst through a tubular reactor maintained at a certain reaction temperature. This system is suitable for achieving a high conversion of the starting materials. Further, when employing an insoluble solid catalyst having a catalyst carried thereon, it is suitable to use a solid bed reaction system wherein the reaction is carried out by passing a solution containing starting materials through the reactor having the catalyst loaded, or it is possible to use a suspension bed reaction system wherein the reaction is carried out by stirring and mixing a solution containing starting materials and a particulate insoluble catalyst in a reactor and maintaining the reaction solution in suspension state.

The reaction temperature is not specially limited so long as it is a temperature at which the catalytic reaction proceeds, but when using a noble metal compound such as palladium, the reaction temperature should not be too high. If the reaction temperature is too high, there is a risk that metallization occurs and an effective catalyst concentration is reduced. Also, if the reaction temperature is too high, there is a risk that the phosphite compound is decomposed. Accordingly, a suitable reaction temperature is usually at least 0° C., preferably at least 20° C., more preferably at least 50° C., and usually at most 180° C., preferably at most 160° C., and more preferably at most 150° C.

The atmosphere in a reactor is preferably filled with a gas inert to the reaction system such as argon or nitrogen, in addition to vapors derived from a solvent, a starting material compound, a reaction product, a reaction by-product, a decomposed material of catalyst and the like. Particularly, it is necessary to pay a special attention so that the atmosphere should not be mixed with oxygen for example by air leakage. If the atmosphere is contaminated with oxygen, the catalyst is degraded and the phosphite compound is decomposed by oxidation. Thus, it is quite necessary to avoid the contamination of the atmosphere with oxygen.

The retention time of the reaction solution in the reactor, i.e. the reaction time, is varied depending on an aimed conversion value of the starting material, but it is necessary to prolong the reaction time if a higher conversion is desired under a constant catalyst concentration. On the other hand, if it is desired to reduce the reaction time by maintaining the high conversion, it is necessary to raise a catalyst activity by raising a catalyst concentration, increasing a catalyst amount or raising the reaction temperature. However, in order to avoid degradation of the catalyst or a side reaction by heat history, it is preferable not to employ unnecessarily long reaction time or high temperature.

In this case, it is preferable for improving a reaction activity to have a phosphonium compound and/or an ammonium compound present in the reaction system.

The phosphonium compound and/or the ammonium compound used in the present invention are not specially limited so long as they have basically a structure wherein four substituents are bonded to a phosphorus atom or a nitrogen atom. By providing such a structure, there is provided a counter cation forming only an ion pair milder than an alkali metal ion which is often conventionally used, and accordingly an attacking property, i.e. reactivity, of a nucleophilic agent can be raised. This is because in the case of an alkali metal ion, +1 valent charge is concentrated on the surface of a small alkali metal ion, whereas in the case of a phosphonium compound or an ammonium compound, the whole molecule is +1 valent and a phosphorus atom or a nitrogen atom having charges concentrated thereon is concealed by four substituents.

Hereinafter, an explanation is made with regard to each compound.

Phosphonium Compound

A phosphonium compound is not specially limited, provided that it is stable under reaction conditions and is solved in the reaction system and does not poison the catalyst (examples of a compound poisoning a catalyst include a compound containing a conjugated diene, a compound oxidizing or decomposing a phosphite compound such as a peroxide, and the like). In view of its solubility in the reaction system, the phosphonium compound has a molecular weight of usually at most 3,000, preferably at most 2,000, more preferably at most 1,500, and usually at least 40, preferably at least 70, more preferably at least 100.

Among them, a phosphonium compound having a structure expressed by the following formula (1) is preferable.

$$PX^1X^2X^3X^4 \qquad (1)$$

In the above formula (1), $X^1$ to $X^4$ are respectively independently a hydrogen atom, a halogen atom, a hydroxyl group, an amino group, a chain-like or cyclic alkyl group, an aryl group (in the present specification, "aryl group" includes a heterocyclic compound forming an aromatic 6Π electron cloud at the upper and lower parts of the ring), an alkoxy group, an aryloxy group, an alkylthio group or an arylthio group. The above illustrated groups may further have a substituent. The substituent is not specially limited so long as it does not adversely affect the reaction system, and preferable examples of the substituent include a halogen atom, a hydroxyl group, an amino group, a chain-like or cyclic alkyl group, an aryl group, an alkoxy group, an aryloxy group, an alkylthio group or an arylthio group. When the above illustrated unsubstituted or substituted groups contain a carbon chain, the carbon chain may have at least one carbon-carbon double bond or triple bond.

The carbon number of $X^1$ to $X^4$ are respectively independently usually at most 40, preferably at most 30, more preferably at most 20. At least two optional groups of $X^1$ to $X^4$ may be bonded to each other to form at least one cyclic structure. The number of cycles is not specially limited, but is usually 0 to 3, preferably 0 to 2, more preferably 0 or 1. When at least two groups of $X^1$ to $X^4$ are bonded to form a cyclic structure, its carbon number is usually at most 40×p, preferably at most 30×p, more preferably at most 20×p, wherein p is the number of groups participating in the formation of a cyclic structure. Also, the number of atoms forming each ring is not specially limited, but is usually 3 to 10-membered ring, preferably 4 to 9-membered ring, more preferably from 5 to 7-membered ring. When a plurality of rings are present, these rings may be partly jointly owned to form a condensed ring structure.

Among the above illustrated groups, preferable examples of $X^1$ to $X^4$ are respectively independently a hydrogen atom, a substituted or unsubstituted chain-like or cyclic alkyl group, an aryl group, an alkoxy group, an arylalkoxy group or an aryloxy group, and more preferable examples include a substituted or unsubstituted chain-like or cyclic alkyl group or an aryl group (in this case also, at least two optional groups of the alkyl group or the aryl group of $X^1$ to $X^4$ may be bonded to form at least one cyclic structure as mentioned above).

Particularly, at least one group of $X^1$ to $X^4$ is preferably a group capable of dispersing +1 valent charge on the phosphorus atom of a phosphonium compound by resonance effect. The phosphonium compound having such a group can provide a counter cation for forming an ion pair. Examples of a group capable of providing such resonance stabilization of cation include a substituted or unsubstituted aryl or a vinyl group, typical example of which include a phenyl group, a 4-methoxyphenyl group, 4-t-butylphenyl group, a 2,4-di-t-butylphenyl group, a 2,4-di-t-butyl-6-methylphenyl group, a 2,5-dimethylphenyl group, a 2,4,6-trimethoxyphenyl group, a 1-naphthyl group, a 2-naphthyl group, a 1-methyl-2-naphthyl group, a vinyl group or a 1-butenyl group. Among them, when taking a strength of effect of resonance stabilization or easy synthesis of a phosphonium compound into consideration, a substituted or unsubstituted aryl group is particularly preferable.

Examples of the phosphonium compound usable in the present invention include hydroxytrimethoxyphosphonium, hydroxymethoxydimethylphosphonium, chlorohydroxydicyclohexylphosphonium, bromotriethoxyphosphonium, trichloro-3-phenoxy-1-propenylphosphonium, dichlorohydroxyphenylphosphonium, tri(t-butoxy)cyclohexylphosphonium, fluorotris(4-methoxyphenyl)phosphonium, methyltri(phenoxy)phosphonium, dimethylaminotris(4-ethylphenyl)phosphonium, tri(ethylthio)hydroxyphosphonium, diethoxyethylphenylthiophosphonium, trifluoromethyltris(dimethylamino)phosphonium, tetra(t-butyl)phosphonium, trimethyl-1-propynylphosphonium, and the like.

Among them, in view of stability and solubility, preferable examples include phosphonium compounds having respectively independently a hydrogen atom, a substituted or unsubstituted chain-like or cyclic alkyl group, an aryl group, an alkoxy group, an arylalkoxy group, an aryloxy group or an alkylaryloxy group as $X^1$ to $X^4$. Typical examples of such phosphonium compounds include tetra(n-dodecyl)phosphonium, tetrakis(2-octenyl)phosphonium, cyclohexyltris(2-methyl-2-butenyl)phosphonium, methoxymethyldi(n-butyl)phosphonium, allyl-t-butylethylphenoxyphosphonium, 4-acetoxy-2-butenylphenylbis(2,4-di-t-butylphenoxy)phosphonium, t-butoxy-3-bromo-1-naphthoxybis(4-nitrophenyl)phosphonium, di(1-naphthoxy)-2,4-di-t-butyl-5-methylphenoxy-2-acetoxy-3-butenylphosphonium, 2-butene-1,4-bis(tris(2-methoxyphenoxy)phosphonium), tetrakis(2,4,6-trimethoxyphenoxy)phosphonium, and the like.

Further, more preferable examples of a phosphonium compound include a compound having a chain-like or cyclic and substituted or unsubstituted alkyl or aryl group as $X^1$ to $X^4$. These preferable examples include a phosphonium compound having a structure wherein all of the four substituents $X^1$ to $X^4$ of the phosphonium compound are bonded to a phosphorus atom by P—C bond. Examples of such a phosphonium compound include tetramethylphosphonium, tetra(n-butyl)phosphonium, tetra(methylol)phosphonium, 4-acetoxybutyldiethyl-2-methoxyethylphosphonium, neopentyltriphenylphosphonium, tetraphenylphosphonium, tetrakis(4-fluorofluorophenyl)phosphonium, 2-butenylbis(4-t-butylphenyl)-3-cyanopropylphosphonium, methyltriphenylphosphonium, 4-methylcyclohexyltri(i-propyl)phosphonium, dimethylpentamethylenephosphonium, 4-acetoxy-2-butenyltriphenylphosphonium, 2-butenyl-1,4-bis(triphenylphosphonium), naphthalene-1,8-bis(trimethylphosphonium), biphenyl-2,2'-bis(diphenylmethylphosphonium), and the like. Also, the examples include all of a phosphonium compound having an allyl group derived from reaction of phosphine and an allyl compound.

Particularly preferable examples include a phosphonium compound wherein at least one of $X^1$ to $X^4$ is a group capable of dispersing +1 valent charge on a phosphorus atom by resonance effect, as mentioned above.

Examples of such a preferable phosphonium compound include trimethylphenylphosphonium, 4-acetoxy-2-butenyldicyclohexylphenylphosphonium, 2-butenyl-1,4-bis(dicyclohexylphenylphosphonium), triethyl-1-naphthylphosphonium, tri-n-butyl-1-methyl-2-naphthylphosphonium, diethylphosphinedrium, 4-acetoxy-2-butenyldiphenyl-i-propylphosphonium, 2-butenyl-1,4-bis(diphenyl-i-propylphosphonium), dimethylbis(2,4-dimethylphenyl)phosphonium, t-butyl-1-acetoxymethyl-2-propenylbis(2-naphthyl)phosphonium, diphenylisophosphinedrium, methyltriphenylphosphonium, 4-acetoxy-2-butenyltriphenylphosphonium, 2-butenyl-1,4-bis(triphenylphosphonium), 1-butene-3,4-bis(triphenylphosphonium), 1-acetoxymethyl-2-propenyltris(4-methoxydiphenyl)phosphonium, tetraphenylphosphonium, di(1-naphthyl)diphenylphosphonium, tetrakis(2-naphthyl)phosphonium, naphthalene-2,6-bis(triphenylphosphonium), and the like.

Further, in order to further weaken cationic property of phosphonium, it is preferable that such an aryl group has an electron donative substituent such as an alkyl group or a methoxy group.

When the above-mentioned phosphonium compound is present in the reaction system of carrying out allylation reaction, an effect of improving a reactivity is achieved. In this case, any one kind of phosphonium compound may be used alone or several kinds of phosphonium compounds may be used by optionally combining and mixing.

A method for introducing the phosphonium compound into the reaction system is not specially limited, but there is a method of positively adding the phosphonium compound to the reaction system or a method of preparing the phosphonium compound in the reaction system. These methods are further explained hereinafter by referring to examples.

First, the method of positively adding the phosphonium compound to the reaction system is a method of feeding the phosphonium compound together with an allyl compound, a nucleophilic agent, a catalyst, a reaction medium and the like to a reactor, and the phosphonium compound may be a new phosphonium compound or a phosphonium compound recycled from the reaction process. In connection with this, it should be noted that since a commercially available phosphonium compound is generally charged with +1 valent charge per one phosphorus atom, it is in a form of salt with its corresponding counter anion, but the counter anion corresponding to phosphonium is preferably a nucleophilic agent reactive with an allyl starting material compound in the reaction system. If the counter anion is not a nucleophilic agent but a phosphonium compound in a form of salt with other counter anion is added, it is desired that the other counter anion does not poison a catalyst and is decomposed by reacting with an allyl compound in the reaction system so that a nucleophilic agent becomes newly a counter anion. Generally known examples of a counter anion of a commercially available phosphonium compound include a halogen atom ion such as chloride, bromide or iodide, and hexafluorophosphate, hexachlorophosphate, hydrogen sulfate, tetrachloroborate, trifluoromethanesulfonate, perchlorate or the like. Among these examples, it is generally considered that there is a high possibility that a halide ion poisons a transition metal catalyst. When using such a halide phosphonium compound, it is preferable to previously remove a halide ion by anion exchange reaction. In this case, it is more preferable to make a nucleophilic agent using a new counter anion in the allylation reaction.

On the other hand, the method of preparing a phosphonium compound in the reaction system includes a method of adding a trivalent phosphorus compound as a starting material for phosphonium. This method uses such a reaction as described in the J. Am. Chem. Soc., 1992, 114, p 6858, and this reaction comprises nucleophilicly attacking a terminal allyl carbon of a Π-allyl complex of transition metal by a trivalent phosphorus compound to form a phosphonium compound having an allyl group newly bonded. Actually, when a production process of 1,4-diacetoxy-2-butene by reaction of 3,4-diacetoxy-1-butene as an allyl starting material compound and acetoxide as a nucleophilic agent in the presence of triphenylphosphine in an amount of 200 equivalents to palladium and palladium-bidentate coordinated phosphite catalyst is analyzed by $^{31}$P-NMR spectrum, a signal of triphenylphosphine of −6 ppm rapidly disappears at the initial stage of reaction and is converted to signals of a plurality of phosphoniums observed at 17 to 25 ppm. Judging from the chemical shift values, these signals are considered to be due to phosphoniums, and the reason why a plurality of kinds are observed, is due to the formation of isomers such as

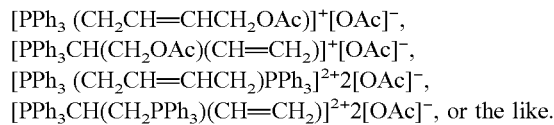

When carrying out such a process, it should be noted that a ligand coordinated to a transition metal compound is eliminated and a catalyst activity is lowered when a coordination power of a trivalent phosphorus compound added as a starting material for phosphonium to a transition metal compound is too high. In such a case, it is necessary to previously convert into a phosphonium compound at the outside of the system before feeding or to wait for slowly converting into a phosphonium compound during carrying out the process.

In view of economic conditions, it is advantageous to use the above phosphonium compound in a small amount. Thus, the phosphonium compound is used to a metal compound as an allylation catalyst (fully described above) at a mol ratio of usually at least 0.1, preferably at least 1, more preferably at least 5, further preferably at least 10, most preferably at least 15, and usually at most 10,000, preferably at most 5,000, more preferably at most 1,000, most preferably at most 500.

Ammonium Compound

An ammonium compound usable in the present invention basically has a structure having four substituents bonded to nitrogen. Usually, the usable ammonium compound is not specially limited so long as it is stable under the reaction conditions and soluble in the reaction system and does not poison a catalyst (examples of a compound poisoning the catalyst include a compound containing a conjugated diene, a compound oxidizing and decomposing a phosphite compound such as a compound containing peroxide, and the like). In view of its solubility in the reaction system, the ammonium compound has a molecular weight usually at most 3,000, preferably at most 2,000, more preferably at most 1,000, and usually at least 20, preferably at least 40, more preferably at least 60.

Among them, an ammonium compound having a structure expressed by the following formula (2) is preferable.

$$NX^1X^2X^3X^4 \quad (2)$$

In the above formula (2), $X^1$ to $X^4$ are respectively independently a hydrogen atom, a halogen atom, a hydroxyl group, an amino group, a chain-like or cyclic alkyl group, an aryl group (in the present specification, "aryl group" includes a heterocyclic compound forming an aromatic 6Π electron cloud at the upper and lower parts of the ring), an alkoxy group, an aryloxy group, an alkylthio group or an arylthio group. The above illustrated groups may further have a substituent. The substituent is not specially limited so long as it does not adversely affect the reaction system, and preferable examples of the substituent include a halogen atom, a hydroxyl group, an amino group, a chain-like or cyclic alkyl group, an aryl group, an alkoxy group, an aryloxy group, an alkylthio group or an arylthio group. When the above illustrated unsubstituted or substituted groups contain a carbon chain, the carbon chain may have at least one carbon-carbon double bond or triple bond.

The carbon number of $X^1$ to $X^4$ are respectively independently usually at most 40, preferably at most 30, more preferably at most 20. At least two optional groups of $X^1$ to $X^4$ may be bonded to each other to form at least one cyclic structure. The number of cycles is not specially limited, but is usually 0 to 3, preferably 0 to 2, more preferably 0 or 1. When at least two groups of $X^1$ to $X^4$ are bonded to form a cyclic structure, its carbon number is usually at most 40×p, preferably at most 30×p, more preferably at most 20×p, wherein p is the number of groups participating in the formation of a cyclic structure. Also, the number of atoms forming each ring is not specially limited, but is usually 3 to 10-membered ring, preferably 4 to 9-membered ring, more preferably from 5 to 7-membered ring. When a plurality of rings are present, these rings may be partly jointly owned to form a condensed ring structure.

Among the above illustrated groups, preferable examples of $X^1$ to $X^4$ are respectively independently a hydrogen atom, a substituted or unsubstituted chain-like or cyclic alkyl group, an aryl group, an alkoxy group, an arylalkoxy group, an aryloxy group or an alkylaryloxy group, and more preferable examples include a substituted or unsubstituted chain-like or cyclic alkyl group or an aryl group (in this case also, at least two optional groups of the alkyl group or the aryl group of $X^1$ to $X^4$ may be bonded to form at least one cyclic structure).

Further, the ammonium compound expressed by the above formula (2) include a compound having an N=C double bond such as N-substituted pyridine, N-substituted oxazolium, N-substituted thiazolium, and the like. Still further, the above ammonium compound includes mono- or polyammonium compounds derived from polyamines such as bidentate chelate type diamines having an amino group as a substituent.

Examples of the ammonium compound usable in the present invention include trimethoxyammonium, methoxydimethyl ammonium, chlorohydroxydicyclohexyl ammonium, bromotriethyl ammonium, dimethylthiodiphenyl ammonium, tri(t-butyl)cyclohexyl ammonium, ethoxytris(4-methoxyphenyl) ammonium, methyltri(phenoxy) ammonium, dimethoxyacetyl ammonium, tri(ethylthio)isopropyl ammonium, diethoxyethylphenylthio ammonium, tetra(n-butyl) ammonium, triethylhydro ammonium, trimethyl-1-propynyl ammonium, N-t-butyl-5-methyloxazolium, 4-methoxypyridinium, N-phenylthiazolium, $Et_2HN$—$CH_2$—$CH_2$—$NEt_2$, $Me_2HN$—$CH_2$—$CH_2$—$CH_2$—$NHMe_2$, $Me_2HN$—$CH_2$—$CH_2$—$NHMe_2$, and the like. In the present specification, Me represents a methyl group and Et represents an ethyl group.

However, generally, compounds easily available and suitably usable in the present invention include the following two types of compounds.

(i) Compounds wherein one of $X^1$ to $X^4$ is a hydrogen atom, and the other three groups are respectively independently a substituted or unsubstituted alkyl or aryl group (at least two optional groups of these alkyl or aryl groups may be bonded to each other to form at least one cyclic structure).

(ii) Compounds wherein all of $X^1$ to $X^4$ are respectively independently a substituted or unsubstituted alkyl or aryl group (at least two optional groups of these alkyl or aryl groups may be bonded to each other to form at least one cyclic structure).

Examples of the above type (i) compound include triethyl ammonium, triisopropyl ammonium, tri-n-dodecyl ammonium, diethylisopropyl ammonium, ethyl-n-propyl-t-butyl ammonium, 3-chloro-1-propyldiphenyl ammonium, triallyl ammonium, geranylbis(4-methoxyphenyl) ammonium, tris(2,4-dimethylphenyl) ammonium, 3-fluorophenyl-2-methylphenyl-2-naphthyl ammonium, tri(2-naphthyl) ammonium, pyridinium, 4-t-butyl ammonium, 4-cyanopyridinium, and compounds expressed by the following formulae (N-1) to (N-6).

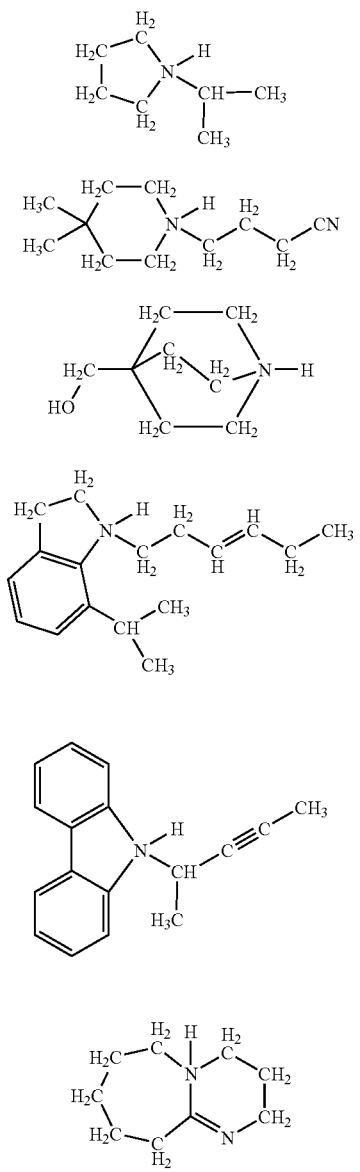

Examples of the above type (ii) compounds include tetramethyl ammonium, tetrabenzyl ammonium, tetraundecenyl ammonium, trimethylethyl ammonium, triallyl-3-pentynyl ammonium, triethylallyl ammonium, diphenylmethylethyl ammonium, trimethyl-2-butenyl ammonium, bis(4-methoxy-1-butyl)diethyl ammonium, di(1-naphthyl)diisopropyl ammonium, t-butylethylisopropyl-4-fluorophenyl ammonium, tris(4-ethylphenyl)-4-acetoxy-2-butenyl ammonium, and compounds expressed by the following formulae (N-7) to (N-12).

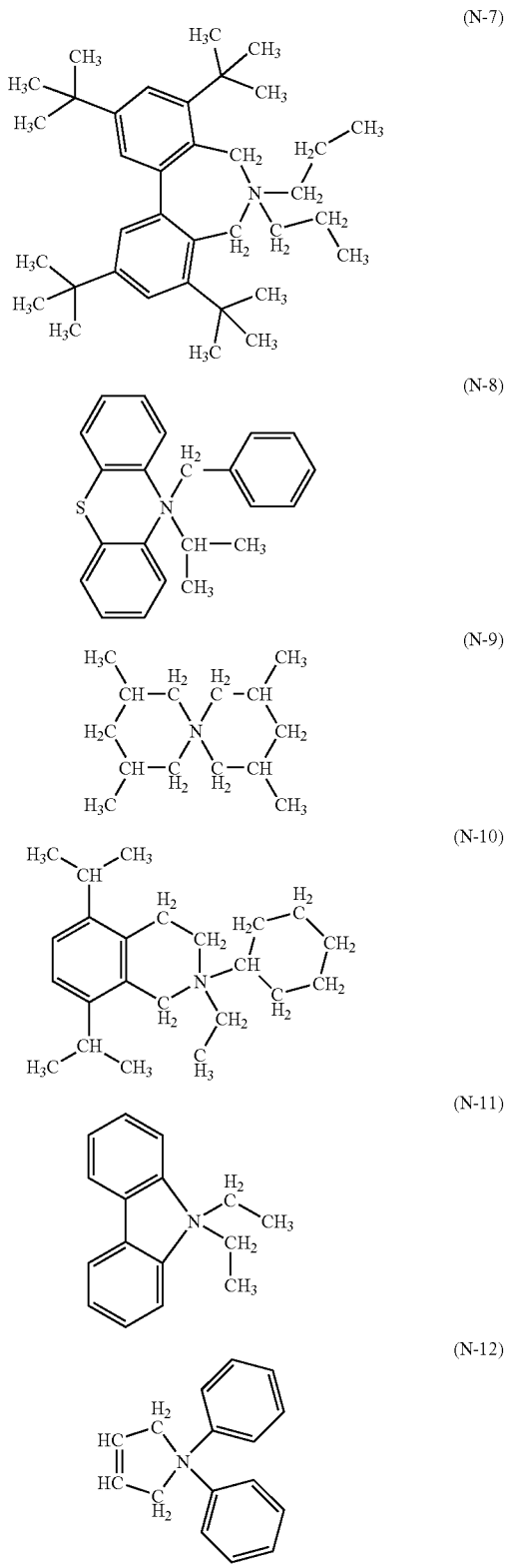

Among the above-mentioned type (i) and type (ii) compounds, an ammonium compound wherein $X^1$ to $X^4$ other than hydrogen are a substituted or unsubstituted alkyl or aryl group is preferable. Examples of such type (i) ammonium compounds include tri-n-octyl ammonium, tris(6-t-butyl-2-naphthyl) ammonium, di-n-propylethylmethyl ammonium, n-propyl-n-butyl-n-pentyl ammonium, 2-chloroethyl-3-methoxypropyl-4-trimethylsilylbutyl ammonium, and the like, and examples of such type (ii) ammonium compounds include tetra-n-nonyl ammonium, tetraphenyl ammonium, diethyldiisopropyl ammonium, triethylbenzyl ammonium, methylethyl-n-propyl-n-butyl ammonium, methyl-t-butyldi (1-naphthyl) ammonium, 5-bromopentyldiethylmethyl ammonium, tris(2,5-dimethylphenyl)-n-octyl ammonium, and the like.

Among the above type (i) and type (ii) ammonium compounds, type (i) ammonium compounds are more preferable from an economical viewpoint since the type (i) ammonium compounds can be easily prepared by acid-base reaction of an acidic material such as acetic acid or phenol and original tertiary amine excluding coordinate-bonded proton. Particularly, type (i) ammonium compounds wherein all of three alkyl groups other than proton are the same are preferable since their production cost is cheap. Examples of such an ammonium compound include an ammonium compound wherein proton is coordinate-bonded to a trialkylamine having the same alkyl groups, such as triethyl ammonium, tri-n-propyl ammonium, triisopropyl ammonium, tri-n-butyl ammonium, tri-sec-butyl ammonium, tri-n-pentyl ammonium, tri-n-neopentyl ammonium, tri-i-octyl ammonium, tri-n-octyl ammonium, tridecanyl ammonium, and the like. Further, an ammonium compound wherein proton is coordinate-bonded to 1,8-diazabicyclo[5.4.0]undecene-7 (DBU) is preferable.

The above-mentioned ammonium compounds achieve an effect of improving a reactivity when they are present in the reaction system of carrying out allylation reaction. In this case, any one kind of ammonium compound may be present alone, or a plurality of kinds of ammonium compounds may be mixed in optional combination.

A method for introducing an ammonium compound into the reaction system is not specially limited, but its examples include a method of positively adding the ammonium compound to the reaction system or a method of preparing the ammonium compound in the reaction system. These methods are further explained by giving concrete examples hereinafter.

First, the method of positively adding the ammonium compound to the reaction system is a method of feeding the ammonium compound together with an allyl compound, a nucleophilic agent, a catalyst, a reaction medium and the like into a reactor, and the ammonium compound may be a new ammonium compound or may be an ammonium compound recycled from the reaction process. In this regard, it should be noted that since a commercially available ammonium compound generally has +1 valent charge per one nitrogen, it takes a form of salt with its corresponding counter anion, but it is preferable that this counter anion corresponding to ammonium is a nucleophilic agent to be reacted with an allyl starting material compound in the reaction system. If the counter anion is not a nucleophilic agent and an ammonium compound in a form of a salt with other counter anion is added, it is desired that the other counter anion does not poison a catalyst and is decomposed by reaction with an allyl compound in the reaction system, and a nucleophilic agent newly becomes a counter anion. Generally known examples of a counter anion of a commercially available ammonium compound include a halide ion such as chloride, bromide or iodide, and hexafluorophosphate, hexachlorophosphate, hydrogen sulfate, tetrachloroborate, trifluoromethane sulfonate, perchlorate and the like. Among them, it is generally considered that there is a high possibility that the halide ion poisons a transition metal catalyst. When such a halogenated ammonium compound is used in the reaction, it is preferable to previously remove it by anionic change reaction or the like. In this case, it is more desirable that a new counter anion is used as a nucleophilic agent to be used for allylation reaction.

On the other hand, examples of the method of preparing an ammonium compound in the reaction system include a method of adding an amine or pyridine compound as a starting material for ammonium. In this method, these compounds showing a basic property causes acid-base reaction with a proton acidic site of a nucleophilic agent in a reactor, and as this result, an ammonium or pyridinium compound having a structure having proton coordinate-bonded to a non-covalent electron pair on nitrogen. When carrying out such a process, it should be noted that when a nucleophilic agent has a proton acidic site, this method can be satisfactorily carried out and achieves a substantial effect particularly in the reaction of an oxygen nucleophilic agent such as phenol or carboxylic acids and a carbon nucleophilic agent such as malonic acid ester derivatives, but when a nucleophilic agent is a nitrogen nucleophilic agent such as amines, a substantial effect can not be achieved since amines are originally basic. Further, it should be noted that when an amine compound added as a starting material for ammonium has an excessively high coordinative power to a transition metal compound, a ligand originally coordinated to a transition metal compound is eliminated and a catalyst activity is lowered. In such a case, it is necessary to previously convert an amine compound into an ammonium compound at the outside of the system before feeding or to wait that an amine compound is gradually converted into an ammonium compound during carrying out the process.

It is advantageous from an economical viewpoint that the above ammonium compound is used in a smaller amount. Thus, the ammonium compound is used in a mol ratio of usually at least 0.1, preferably at least 1, more preferably at least 5, further preferably at least 10, most preferably at least 15, and usually at most 10,000, preferably at most 5,000, more preferably at most 1,000, most preferably at most 500, to a metal compound as an allylation reaction catalyst as fully illustrated above.

Also, many separating operations used in a conventional liquid catalyst recycling process can be employed for separating a catalyst and an allyl compound obtained in the reaction. Examples of the separating operations include distillation operations such as simple distillation, vacuum distillation, thin film distillation, water vapor distillation or the like, and other separating operations such as gas-liquid separation, evaporation, gas stripping, gas absorption and extraction. The separating operation of each component may be carried out respectively in an independent step, or separation of two or more components may be carried out at the same time in a single step. When a part of an allyl starting material compound or an unreacted nucleophilic agent remains, they may be recovered by a separating method in the same manner as above and may be recycled into a reactor, which provides an economical advantage. Further, it is economically desirable to recycle the separated catalyst into the reactor as it is or to recover the separated catalyst to be reactivated for reuse.

EXAMPLES

Hereinafter, the present invention is further fully illustrated by the following Examples, but should not be limited thereto.

Example 1 and Comparative Example 1

Allylphenyl ether synthesis reaction of the present invention was carried out by using allylmethyl carbonate as an allyl starting material compound and phenol as an oxygen nucleophilic agent.

A catalyst solution having a palladium concentration of 15.05 mmol/l was prepared by adding 0.0149 g (0.0151 mmol) of trisdibenzylideneacetone dipalladium having a palladium content of 21.5 wt % as a transition metal compound and the above (L-6) bidentate phosphite (Example 1) in an amount of 4 equivalents (0.1204 mmol) to palladium as a bidentate coordinated phosphite compound to a container substituted with argon, adding 2.0 ml of tetrahydrofuran thereto and stirring the resultant mixture at room temperature. Thereafter, in order to carry out the reaction, another container was substituted with argon, and 5.0 ml of a tetrahydrofuran solution containing 0.1720 g (1.481 mmol) of allylmethyl carbonate and 0.2707 g (2.877 mmol) of phenol was added into the container under argon atmosphere. 20.0 μl of the above prepared catalyst solution was added thereto by a microsyringe, and the resultant mixture was heated at 60° C. to carry out the reaction. After reacting for 30 minutes, the resultant solution composition was analyzed by gas chromatography to determine a yield of allylphenyl ether.

As Comparative Example, the same procedure was repeated by using a bidentate phosphite ligand having a structure of the following formula (L-A) (Comparative Example 1).

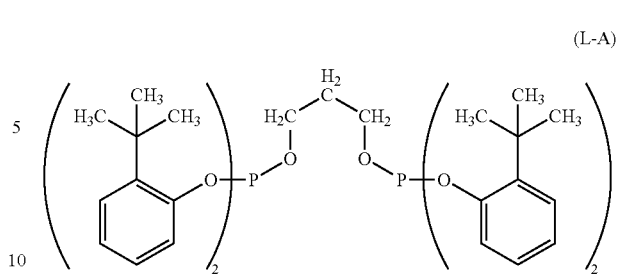

The results are shown in the following Table 1.

TABLE 1

| | Ligand | Allylphenyl ether yield |
| --- | --- | --- |
| Ex. 1 | (L-6) | 89% |
| Comp. Ex. 1 | (L-A) | 10% |

Examples 2, 3 and Comparative Example 2

Allyloctyl ether synthesis reaction of the present invention was carried out by using allyl acetate as an is allyl starting material compound and 1-octanol as an oxygen nucleophilic agent.

The reaction was carried out by adding 0.0048 g (0.0048 mmol) of trisdibenzylideneacetone dipalladium having a palladium content of 21.5 wt % as a transition metal compound and the above (L-6) bidentate phosphite compound (Example 2) or the above (L-13) bidentate phosphite compound (Example 3) respectively in an amount of 2 equivalents (0.0194 mmol) to palladium as a bidentate coordinated phosphite compound to a container substituted with argon, adding 0.943 g (9.420 mmol) of allyl acetate and 2.422 g (18.594 mmol) of 1-octanol under argon atmosphere thereto, and heating the resultant mixture at 100° C. to carry out the reaction. After reacting for 60 minutes, the resultant solution composition was analyzed by gas chromatography to determine a yield of allyloctyl ether.

Also, as Comparative Example, the same reaction procedure was repeated by using a bidentate phosphite ligand having a structure of the following formula (L-B) (Comparative Example 2).

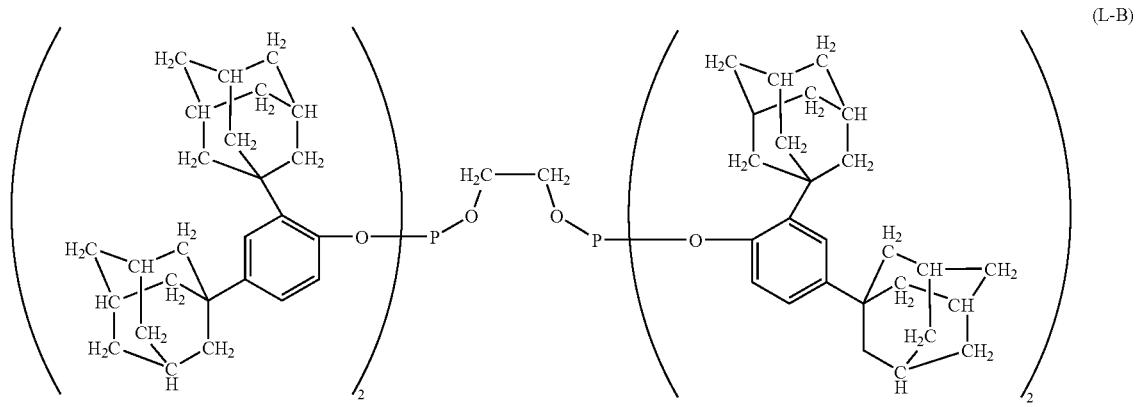

The results are shown in the following Table 2.

TABLE 2

| | Ligand | Allyloctyl ether yield |
|---|---|---|
| Ex. 2 | (L-6) | 91% |
| Ex. 3 | (L-13) | 92% |
| Comp. Ex. 2 | (L-B) | 82% |

Example 4 and Comparative Example 3

Allyl benzoate synthesis reaction of the present invention was carried out by using allyl acetate as an allyl starting material compound and benzoic acid as an oxygen nucleophilic agent.

A catalyst solution having a palladium concentration of 15.05 mmol/l was prepared by adding 0.0149 g (0.0151 mmol) of trisdibenzylideneacetone dipalladium having a palladium content of 21.5 wt % as a transition metal compound and the above (L-11) bidentate phosphite compound (Example 4) in an amount of 4 equivalents (0.1204 mmol) to palladium as a bidentate coordinated phosphite compound to a container substituted with argon, adding 2.0 ml of tetrahydrofuran thereto, and stirring the resultant mixture at room temperature. Thereafter, in order to carry out the reaction, another container was substituted with argon, and 4.0 ml of a tetrahydrofuran solution containing 0.3083 g (2.525 mmol) of benzoic acid and 0.1208 g (1.206 mmol) of allyl acetate was added thereto under argon atmosphere. 60.0 μl of the above prepared catalyst solution was added thereto by a microsyringe, and the resultant mixture was heated at 60° C. to carry out the reaction. After reacting for 30 minutes, the resultant solution composition was analyzed by gas chromatography to determine a yield of allyl benzoate.

Also, as Comparative Example, the same reaction procedure was repeated by using a bidentate phosphite ligand having a structure of the following formula (L-C) (Comparative Example 3).

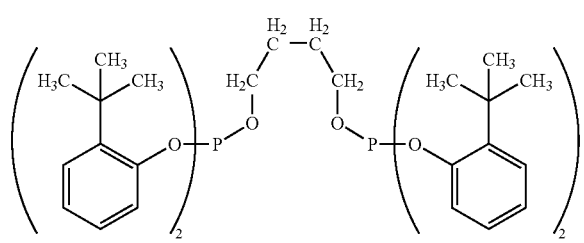

(L-C)

The results are shown in the following Table 3.

TABLE 3

| | Ligand | Allyl benzoate yield |
|---|---|---|
| Ex. 4 | (L-11) | 42% |
| Comp. Ex. 3 | (L-C) | 38% |

Example 5 and Comparative Example 4

Allyl dicyclohexyl amine synthesis reaction of the present invention was carried out by using allyl acetate as an allyl starting material compound and dicyclohexyl amine as an oxygen nucleophilic agent.

The reaction was carried out by adding 0.0014 g (0.00141 mmol) of trisdibenzylideneacetone dipalladium having a palladium content of 21.5 wt % as a transition metal compound and the above (L-6) bidentate phosphite compound (Example 5) in an amount of 4 equivalents (0.0113 mmol) to palladium as a bidentate coordinated phosphite compound to a container substituted with argon, adding 3.0 ml of a tetrahydrofuran solution containing 0.0821 g (0.820 mmol) of allyl acetate and 0.2992 g (1.650 mmol) of dicyclohexyl amine thereto, and reacting the resultant mixture at 25° C. After reacting for 6 minutes, the resultant solution composition was analyzed by gas chromatography to determine a yield of allyl dicyclohexyl amine.

Also, as Comparative Example, the same reaction procedure was repeated by using a bidentate phosphine ligand having a structure of the above formula (L-B) (Comparative Example 4).

The results are shown in the following Table 4.

TABLE 4

| | Ligand | Allyldicyclohexylamine yield |
|---|---|---|
| Ex. 5 | (L-6) | 13% |
| Comp. Ex. 4 | (L-B) | 2% |

Example 6

Butylbutenyl ethers synthesis reaction of the present invention was carried out by using cis-1,4-diacetoxy-2-butene as an allyl starting material compound and 1-butanol as an oxygen nucleophilic agent.

The reaction was carried out by adding 0.0020 g (0.0040 mmol) of trisdibenzylideneacetone dipalladium having a palladium content of 21.5 wt % and 0.0173 g (0.0162 mmol) of the above (L-6) bidentate phosphite in an amount of 4 equivalents to a container substituted with nitrogen, adding 1.418 g (8.233 mmol) of cis-1,4-diacetoxy-2-butene and 2.327 g (31.395 mmol) of 1-butanol thereto under nitrogen atmosphere, and heating the resultant mixture at 100° C. After reacting 5 hours, the resultant solution composition was analyzed by gas chromatography, and it was found that cis-1,4-diacetoxy-2-butene was converted at a conversion rate of 97.5%, and 71.8% of dibutoxybutene and 25.7% of acetoxybutoxybutene were produced.

Particularly, among the 71.8% dibutoxybutene thus produced, 56.0% of 1,4-dibutoxy-2-butene (mixture of cis and trans) and 15.8% of 3,4-dibutoxy-1-butene were formed, and among the 25.7% acetoxybutoxybutene thus produced, 12.6% of 1-acetoxy-4-butoxy-2-butene (mixture of cis and trans), 4.9% of 3-acetoxy-4-butoxy-1-butene and 8.2% of 4-acetoxy-3-butoxy-1-butene were formed.

Example 7

Phenylbutenyl ethers synthesis reaction of the present invention was carried out by using cis-1,4-diacetoxy-2-butene as an allyl starting material compound and phenol as an oxygen nucleophilic agent.

The reaction was carried out by adding 0.0020 g (0.0044 mmol) of trisdibenzylideneacetone dipalladium having a palladium content of 21.5 wt % and 0.0187 g (0.0175 mmol) of the above (L-6) bidentate phosphite in an amount of 4 equivalents to a container substituted with nitrogen, adding 1.460 g (8.477 mmol) of cis-1,4-diacetoxy-2-butene and 3.164 g (33.615 mmol) of phenol thereto under nitrogen atmosphere, and heating the resultant mixture at 100° C.

After reacting 60 minutes, the resultant solution composition was analyzed by gas chromatography, and it was found that cis-1,4-diacetoxy-2-butene was converted at a conversion rate of 75.2%, and 14.9% of dephenoxy and 59.8% of acetoxyphenoxybutene were produced.

Particularly, among the 14.9% diphenoxybutene thus produced, 13.9% of 1,4-diphenoxy-2-butene (mixture of cis and trans) and 1.0% of 3,4-diphenoxy-1-butene were formed, and among the 59.8% acetoxyphenoxybutene thus produced, 37.8% of 1-acetoxy-4-phenoxy-2-butene (mixture of cis and trans), 11.1% of 3-acetoxy-4-phenoxy-1-butene and 10.9% of 4-acetoxy-3-phenoxy-1-butene were formed.

Example 8

The present invention was applied to synthesis reaction of an unsaturated bond-containing polyester oligomer by using cis-1,4-diacetoxy-2-butene as an allyl starting material compound and adipic acid (difunctional carboxylic acid) as an oxygen nucleophilic agent.

The reaction was carried out by adding 0.0074 g (0.0162 mmol) of trisdibenzylideneacetone dipalladium having a palladium content of 21.5 wt % and 0.0693 g (0.0647 mmol) of the above (L-6) bidentate phosphite in an amount of 4 equivalents to a two-forked round bottom flask substituted with nitrogen, adding 10.005 g (58.107 mmol) of cis-1,4-diacetoxy-2-butene and 7.104 g (48.610 mmol) of adipic acid thereto under nitrogen atmosphere, and heating the resultant mixture at 100° C. under a reduced pressure of 50 mmHg. As the reaction proceeds, the pressure in the system was gradually lowered to 20 mmHg (after 1 hour) and to 7 mmHg (after three hours), and acetic acid formed was removed from the system under the reduced pressure by distillation. After reacting for 7 hours, the resultant solution composition was analyzed by gas chromatography, and it was found that cis-1,4-diacetoxy-2-butene was converted at a conversion rate of almost 100% to obtain a syrup-like oligomer. The oligomer thus obtained was analyzed by gel permeation chromatography to determine a molecular weight distribution, and it was found that the oligomer was a polyester oligomer having a molecular weight of 4,000 at the main central portion and a maximum molecular weight of 10,000 in terms of polystyrene molecular weight.

Example 9

The present invention was applied to synthesis reaction of an unsaturated bond-containing polyether oligomer by using cis-1,4-diacetoxy-2-butene as an allyl starting material compound and 1,4-butane diol (difunctional alcohol) as an oxygen nucleophilic agent.

The reaction was carried out by adding 0.0572 g (0.1249 mmol) of trisdibenzylideneacetone dipalladium having a palladium content of 21.5 wt % and 0.2670 g (0.2492 mmol) of the above (L-6) bidentate phosphite in an amount of 2 equivalents to a two-forked round bottom flask substituted with nitrogen, adding 17.221 g (100.016 mmol) of cis-1,4-diacetoxy-2-butene and 9.012 g (100.000 mmol) of 1,4-butane diol thereto under nitrogen atmosphere, and heating the resultant mixture at 100° C. while gradually reducing a pressure from 50 mmHg in the same manner as in Example 8. After reacting for 7 hours, the resultant solution composition was analyzed by gas chromatography, and it was found that cis-1,4-diacetoxy-2-butene was converted at a conversion rate of almost 100% to obtain a syrup-like oligomer. The oligomer thus obtained was analyzed by gel permeation chromatography to determine a molecular weight distribution, and it was found that the oligomer was a polyether oligomer having a molecular weight of 2,400 at the main central portion and a maximum molecular weight of 7,000 in terms of polystyrene molecular weight.

Example 10

The present invention was applied to synthesis reaction of an unsaturated bond-containing polyether oligomer by using cis-1,4-diacetoxy-2-butene as an allyl starting material compound and 2,2-bis(4-hydroxyphenyl)propane (difunctional phenol: bisphenol A) as an oxygen nucleophilic agent.

The reaction was carried out by adding 0.0091 g (0.0199 mmol) of trisdibenzylideneacetone dipalladium having a palladium content of 21.5 wt % and 0.0852 g (0.0795 mmol) of the above (L-6) bidentate phosphite in an amount of 4 equivalents to a two-forked round bottom flask substituted with nitrogen, adding 10.008 g (58.126 mmol) of cis-1,4-diacetoxy-2-butene and 11.001 g (48.189 mmol) of bisphenol A thereto under nitrogen atmosphere, and heating the resultant mixture at 100° C. while gradually reducing a pressure from 50 mmHg in the same manner as in Example 8. After reacting for 7 hours, the resultant solution composition was analyzed by gas chromatography, and it was found that cis-1,4-diacetoxy-2-butene was converted at a conversion rate of almost 100% to obtain a thick syrup-like oligomer. The oligomer thus obtained was analyzed by gel permeation chromatography to determine a molecular weight distribution, and it was found that the oligomer was a polyether oligomer having a molecular weight of 3,200 at the main central portion and a maximum molecular weight of 7,000 in terms of polystyrene molecular weight.

As evident from the above results, a catalyst comprising the bidentate phosphite type ligand (the carbon atom of P—O—C bond in the crosslinking group is a $SP^2$ carbon derived from an aryl group) of the present invention provides a higher catalytic activity as compared with that of a catalyst comprising conventionally used bidentate phosphine type ligand (the carbon atom of P—O—C bond in the crosslinking group is a $SP^3$ carbon derived from an alkyl group).

(Examples 11 and 12: Examples using a phosphonium compound in the reaction system are illustrated below.)

Example 11 and Example 12

The present invention was applied to a reaction for producing allylphenyl ether by carrying out allylation reaction by using allylmethyl carbonate as an allyl starting material compound and phenoxide as a nucleophilic agent in the presence of a catalyst of palladium-bidentate phosphite (L-6).

A catalyst solution having a palladium concentration of 15.05 mmol/l was prepared by adding 0.0149 g (0.0151 mmol) of trisdibenzylideneacetone dipalladium having a palladium content of 21.5 wt % as a transition metal compound and 0.1291 g (0.1205 mmol) of the above (L-6) compound as a bidentate phosphite compound to a container substituted with argon, adding 2.0 ml of tetrahydrofuran thereto, and stirring the resultant mixture at room temperature. Thereafter, in order to carry out the reaction, another container was substituted with argon, and 4.45 g of a tetrahydrofuran solution containing 3.85 wt % of allylmethyl carbonate and 6.06 wt % of phenol was added into the container. 5 µl of the above prepared catalyst solution was added thereto by a microsyringe, and the resultant mixture was heated at 60° C. to carry out the reaction (Example 11: reaction in the absence of a phosphonium compound). Evaluation of the reaction rate was carried out by analyzing the solution composition by gas chromatography before and after the reaction to determine a conversion rate of allylmethyl carbonate, and applying the value thus determined to the following calculation formula to calculate a reaction rate constant. In this case, the reaction is considered to be a pseudo-primary reaction by ignoring an influence by a concentration change of phenol to calculate a reaction rate: k in accordance with the following calculation formula. In the following calculation formula, conv. represents a conversion rate of allylmethyl carbonate and t represents its reaction time (unit: hour).

$k = -\ln(1-\text{conv.})/t$

Also, a reaction was carried out in a system of further containing tetra(n-butyl)phosphonium acetate salt respectively in an amount of 200 equivalents to Pd under the same conditions as in the above Example 11 (Example 12: the reaction system in the presence of a phosphonium compound).

The results are shown in the following Table 5.

TABLE 5

|        | Phosphonium compound | Reaction rate constant (h$^{-1}$) | Specific activity |
|--------|----------------------|-----------------------------------|-------------------|
| Ex. 11 | —                    | 0.59                              | 1.00              |
| Ex. 12 | [P(n-Bu)$_4$]$^+$[OAc]$^-$ | 1.81                        | 3.07              |

As evident from the above results, it is proved that the presence of a phosphonium compound in the reaction system can improve the reaction activity.

(Examples 13 to 14: Examples using an ammonium compound are illustrated below.)

Example 13 and Example 14

The present invention was applied to a reaction for producing allylphenyl ether by carrying out allylation reaction by using allylmethyl carbonate as an allyl starting material compound and phenoxide as a nucleophilic agent in the presence of a catalyst of palladium-bidentate phosphite (L-6).

A catalyst solution having a palladium concentration of 15.05 mmol/l was prepared by adding 0.0149 g (0.0151 mmol) of trisdibenzylideneacetone dipalladium having a palladium content of 21.5 wt % as a transition metal compound and 0.1291 g (0.1205 mmol) of the above (L-6) compound as a bidentate phosphite compound to a container substituted with argon, adding 2.0 ml of tetrahydrofuran thereto, and stirring the resultant mixture at room temperature. Thereafter, in order to carry out the reaction, another container was substituted with argon, and 4.45 g of a tetrahydrofuran solution containing 3.85 wt % of allylmethyl carbonate and 6.06 wt % of phenol was added into the container. 5 µl of the above prepared catalyst solution was added thereto by a microsyringe, and the resultant mixture was heated at 60° C. to carry out the reaction (Example 13: reaction in the absence of a counter cation). Evaluation of the reaction rate was carried out in the same manner as in Examples 11 and 12.

Also, a reaction was carried out in a system of further adding DBU in an amount of 200 equivalents to palladium to prepare an ammonium compound under the same conditions as in the above Example 13 (Example 14: the reaction system in the presence of an ammonium compound).

The results are shown in the following Table 6.

TABLE 6

|        | Ammonium compound | Reaction rate constant (h$^{-1}$) | Specific activity |
|--------|-------------------|-----------------------------------|-------------------|
| Ex. 13 | —                 | 0.59                              | 1.00              |
| Ex. 14 | [DBU-H]$^+$[OAc]$^-$ | 1.51                           | 2.56              |

As evident from the above results, it is proved that the presence of an ammonium compound in the reaction system can improve the reaction activity.

According to the production method of an allyl compound of the present invention, various kinds of allyl compounds can be efficiently produced and industrial advantages can be provided as compared with conventional catalyst systems since a new catalyst system produced cheaply, having an excellent thermal stability and achieving a high catalyst activity is employed in the production of a new allyl compound by reacting an allyl starting material compound and a nucleophilic agent.

Further, a catalyst activity can be quite easily enhanced and the production efficiency of an allyl compound can be largely improved, thereby providing industrial advantages, since a catalyst comprising a transition metal compound of Group 8 to Group 10 of the Periodic Table and a bidentate phosphite compound of a specific structure is employed in the production of a new allyl compound by reacting an allyl starting material compound and a nucleophilic agent.

The entire disclosures of Japanese Patent Application No. 2002-252901 filed on Aug. 30, 2002, Japanese Patent Application No. 2002-260452 filed on Sep. 5, 2002 and Japanese Patent Application No. 2002-261870 filed on Sep. 6, 2002 including specifications, claims and summaries are incorporated herein by reference in their entireties.

What is claimed is:

1. A method for producing an allyl compound having a formula different from that of an allyl starting compound, which comprises reacting the allyl starting compound with a nucleophilic agent in the presence of a catalyst containing at least one transition metal compound containing a transition metal selected from the group consisting of elements belonging to Group 8 to Group 10 of the Periodic Table and at least one bidentate coordinated phosphite compound selected from the group consisting of compounds having the following formulae (I) to (III):

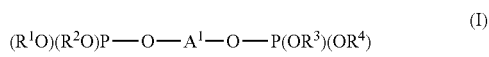

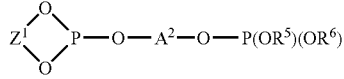

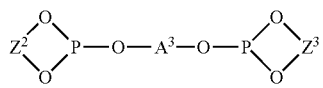
(III)

wherein $A^1$ to $A^3$ are respectively independently a diarylene group having a branched alkyl group at the ortho-position, $R^1$ to $R^6$ are respectively independently an optionally substituted alkyl group or an aryl group which may have a substituent which may be a heterocyclic compound that forms an aromatic 6π electron cloud on the upper and lower sides of the ring, and $Z^1$ to $Z^3$ are respectively independently an optionally substituted alkylene group, an optionally substituted arylene group, an optionally substituted alkylene-arylene group or an optionally substituted diarylene group.

2. The method for producing an allyl compound according to claim 1, wherein the allyl starting compound has the following formula (a):

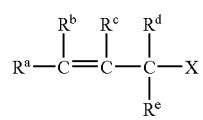
(a)

wherein $R^a$ to $R^e$ are respectively independently a hydrogen atom, a halogen atom, a hydroxyl group, an amino group, an alkyl group, an aryl group, an alkoxy group, an aryloxy group, an alkylthio group, an arylthio group, an acyl group or an acyloxy group; and among these groups, the amino group, the alkyl group, the aryl group, the alkoxy group, the aryloxy group, the alkylthio group, the arylthio group, the acyl group or the acyloxy group are optionally substituted; and when any of $R^a$ to $R^e$ has a carbon chain, the carbon chain optionally has at least one carbon-carbon double bond or triple bond;

X is a halogen atom, a hydroxyl group, a nitro group, an amino group, a sulfonyl group, a sulfonate group, an acyloxy group, a carbonate group, a carbamate group, a phosphate group, an alkoxy group or an aryloxy group; and among these groups, the amino group, the sulfonyl group, the sulfonate group, the acyloxy group, the carbonate group, the carbamate group, the phosphate group, the alkoxy group and the aryloxy group are optionally substituted; and when X has a carbon chain, the carbon chain optionally has at least one carbon-carbon double bond or triple bond; and at least two optional groups among $R^a$ to $R^e$ and X are bonded to each other to form at least one cyclic structure.

3. The method for producing an allyl compound according to claim 1, wherein the transition metal compound is at least one compound selected from the group consisting of a ruthenium compound, a rhodium compound, an iridium compound, a nickel compound, a palladium compound and a platinum compound.

4. The method for producing an allyl compound according to claim 1, wherein in formulae (I) to (III), $R^1$ to $R^6$ are respectively independently an optionally substituted $C_6$–$C_{20}$ aryl group, and $Z^1$ to $Z^3$ are respectively independently an optionally substituted diarylene group.

5. The method for producing an allyl compound according to claim 1, wherein in formulae (I) to (III), $A^1$ to $A^3$ are respectively independently an optionally substituted diarylene group having the following formula (IV) or (V):

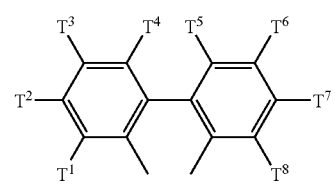
(IV)

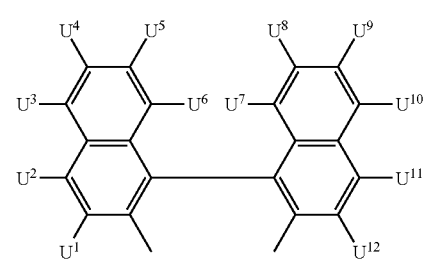
(V)

wherein $T^1$, $T^8$, $U^{12}$ are respectively independently a branched alkyl group, and $T^2$ to $T^7$ and $U^2$ to $U^{11}$ are respectively independently a hydrogen atom, a halogen atom, an alkyl group, an aryl group, an alkoxy group, an aryloxy group, an acyl group, an acyloxy group, an imino group, an ester group, a carboxy group or a hydroxyl group.

6. The method for producing an allyl compound according to claim 5, wherein $T^2$ to $T^7$ and $U^2$ to $U^{11}$ are respectively independently a hydrogen atom, an alkyl group which may have a substituent, an optionally substituted alkoxy group or an optionally substituted aryl group.

7. The method for producing an allyl compound according to claim 1, wherein $Z^1$ to $Z^3$ are respectively independently a diarylene group of the following formula (VI) or (VII) which may have a substituent:

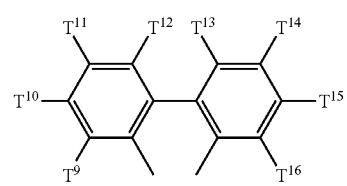
(VI)

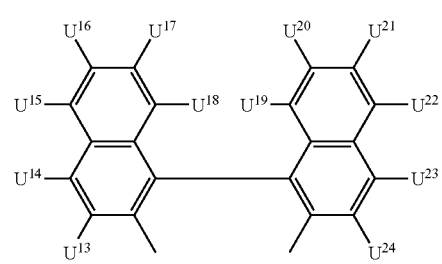
(VII)

wherein $T^9$ to $T^{16}$ and $U^{13}$ to $U^{24}$ are respectively independently a hydrogen atom, a halogen atom, an alkyl group, an aryl group, an alkoxy group, an aryloxy group, an acyl group, an acyloxy group, an amino group, an ester group, a carboxy group or a hydroxyl group.

8. The method for producing an allyl compound according to claim 1, wherein a phosphonium compound is present in the reaction system.

9. The method for producing an allyl compound according to claim 1, wherein an ammonium compound is present in the reaction system.

10. The method for producing an allyl compound according to claim 1, wherein the transition metal compound is present in the reaction system in an amount of at least $1\times10^{-8}$ mole equivalent relative to the amount of starting allyl compound.

11. The method for producing an allyl compound according to claim 10, wherein the amount of said transition metal compound is at least $1\times10^{-7}$ mole equivalent.

12. The method for producing an allyl compound according to claim 1, wherein said bidentate phosphite compound is present in the reaction system in an amount determined by a mole ratio of at least 0.1 relative to the amount of the transition metal compound that is present.

13. The method for producing an allyl compound according to claim 12, wherein the molar ratio of the bidentate phosphite compound to the transition metal compound is at least 0.5.

* * * * *